(12) United States Patent
Bonutti et al.

(10) Patent No.: US 9,463,012 B2
(45) Date of Patent: Oct. 11, 2016

(54) APPARATUS FOR GUIDING AND POSITIONING AN IMPLANT

(75) Inventors: Peter M. Bonutti, Effingham, IL (US); Glen A. Phillips, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 955 days.

(21) Appl. No.: 11/202,294

(22) Filed: Oct. 5, 2005

(65) Prior Publication Data

US 2007/0088362 A1 Apr. 19, 2007

(51) Int. Cl.
| | | |
|---|---|---|
| *A61F 2/00* | (2006.01) | |
| *A61B 17/04* | (2006.01) | |
| *A61B 17/02* | (2006.01) | |
| *A61B 17/68* | (2006.01) | |
| *A61B 17/88* | (2006.01) | |
| *A61B 17/16* | (2006.01) | |
| *A61B 17/70* | (2006.01) | |
| *A61B 17/84* | (2006.01) | |
| *A61B 17/29* | (2006.01) | |
| *A61F 2/08* | (2006.01) | |
| *A61F 2/28* | (2006.01) | |

(Continued)

(52) U.S. Cl.
CPC ....... *A61B 17/0482* (2013.01); *A61B 17/0218* (2013.01); *A61B 17/0469* (2013.01); *A61B 17/683* (2013.01); *A61B 17/8869* (2013.01); *A61B 17/1615* (2013.01); *A61B 17/7053* (2013.01); *A61B 17/842* (2013.01); *A61B 2017/0409* (2013.01); *A61B 2017/2926* (2013.01); *A61F 2/08* (2013.01); *A61F 2/28* (2013.01); *A61F 2/442* (2013.01); *A61F 2002/2817* (2013.01); *A61F 2002/30062* (2013.01); *A61F 2002/30677* (2013.01); *A61F 2002/444* (2013.01); *A61F 2002/4435* (2013.01); *A61F 2210/0004* (2013.01); *A61F 2310/00293* (2013.01)

(58) Field of Classification Search
CPC .................................................. A61B 17/0482
USPC ......... 606/86 R, 96, 99, 104, 139, 148, 147, 606/144, 232
See application file for complete search history.

(56) References Cited

U.S. PATENT DOCUMENTS

| | | |
|---|---|---|
| 319,296 A | 6/1885 | Molesworth |
| 668,878 A | 2/1901 | Jensen |
| 668,879 A | 2/1901 | Miller |

(Continued)

FOREIGN PATENT DOCUMENTS

| | | |
|---|---|---|
| CA | 2641580 | 8/2007 |
| CA | 2680827 | 9/2008 |

(Continued)

OTHER PUBLICATIONS

Copending U.S. Appl. No. 11/456,132, filed Jul. 7, 2006.

(Continued)

*Primary Examiner* — Christian Sevilla

(57) ABSTRACT

An implant guidance and positioning device is provided for dynamic and rigid fixation of tissue or an implant. The device includes a handle and an elongated hook connected with the handle, which may have a lumen extending therethrough or may have a socket that can receive fasteners. The device also includes a guide channel or slot disposed in the handle. The longitudinal axis of the guide channel or slot may be generally aligned with or slightly offset from a distal end of the elongated hook or socket.

12 Claims, 12 Drawing Sheets

(51) Int. Cl.
*A61F 2/44* (2006.01)
*A61F 2/30* (2006.01)

(56) References Cited

U.S. PATENT DOCUMENTS

| | | |
|---|---|---|
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1939 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss et al. |
| 3,347,234 A | 10/1967 | Voss |
| 3,367,809 A | 2/1968 | Soloff |
| 3,391,690 A | 7/1968 | Armao |
| 3,477,429 A * | 11/1969 | Sampson ................. 606/86 R |
| 3,513,848 A * | 5/1970 | Winston ................. 606/228 |
| 3,518,993 A | 7/1970 | Blake |
| 3,577,991 A | 5/1971 | Wilkinson |
| 3,596,292 A | 8/1971 | Erb et al. |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,678,980 A | 7/1972 | Gutshall |
| 3,709,218 A | 1/1973 | Halloran |
| 3,711,347 A | 1/1973 | Wagner et al. |
| 3,760,808 A | 9/1973 | Bleuer |
| 3,788,318 A | 1/1974 | Kim et al. |
| 3,789,852 A | 2/1974 | Kim et al. |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee et al. |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A * | 2/1975 | Huene ................. 606/80 |
| 3,875,652 A | 4/1975 | Arnold |
| 3,898,992 A | 8/1975 | Balamuth |
| 3,918,442 A | 11/1975 | Nikolaev et al. |
| 3,968,800 A | 7/1976 | Vilasi |
| 4,023,559 A | 5/1977 | Gaskell |
| 4,064,566 A | 12/1977 | Fletcher et al. |
| 4,089,071 A | 5/1978 | Kainberz et al. |
| 4,156,574 A | 5/1979 | Boden |
| 4,164,794 A | 8/1979 | Spector et al. |
| 4,171,544 A | 10/1979 | Hench et al. |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu et al. |
| 4,257,411 A | 3/1981 | Cho |
| 4,265,231 A | 5/1981 | Scheller, Jr. et al. |
| 4,281,649 A | 8/1981 | Derweduwen |
| 4,291,698 A | 9/1981 | Fuchs |
| 4,309,488 A | 1/1982 | Heide et al. |
| 4,320,762 A | 3/1982 | Bentov |
| 4,351,069 A | 9/1982 | Ballintyn et al. |
| 4,364,381 A | 12/1982 | Sher et al. |
| 4,365,356 A | 12/1982 | Broemer et al. |
| 4,388,921 A | 6/1983 | Sutter et al. |
| 4,395,798 A | 8/1983 | McVey |
| 4,409,974 A | 10/1983 | Freedland |
| 4,414,166 A | 11/1983 | Charlson et al. |
| 4,437,191 A | 3/1984 | Van der Zel et al. |
| 4,437,362 A | 3/1984 | Hurst |
| 4,444,180 A | 4/1984 | Schneider et al. |
| 4,448,194 A | 5/1984 | DiGiovanni et al. |
| 4,456,005 A | 6/1984 | Lichty |
| 4,461,281 A | 7/1984 | Carson |
| 4,493,317 A | 1/1985 | Klaue |
| 4,495,664 A | 1/1985 | Blanquaert |
| 4,501,031 A | 2/1985 | McDaniel et al. |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins et al. |
| 4,556,350 A | 12/1985 | Bernhardt et al. |
| 4,566,138 A | 1/1986 | Lewis et al. |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,606,335 A | 8/1986 | Wedeen |
| 4,621,640 A | 11/1986 | Mulhollan et al. |
| 4,630,609 A | 12/1986 | Chin |
| 4,632,100 A | 12/1986 | Somers |
| 4,632,101 A | 12/1986 | Freedland |
| 4,645,503 A | 2/1987 | Lin et al. |
| 4,657,460 A | 4/1987 | Bien |
| 4,659,268 A | 4/1987 | Del Mundo et al. |
| 4,662,063 A | 5/1987 | Collins et al. |
| 4,662,068 A | 5/1987 | Polonsky |
| 4,662,887 A | 5/1987 | Turner et al. |
| 4,669,473 A | 6/1987 | Richards et al. |
| 4,685,458 A | 8/1987 | Leckrone |
| 4,691,741 A | 9/1987 | Affa |
| 4,705,040 A | 11/1987 | Mueller et al. |
| 4,706,670 A | 11/1987 | Andersen et al. |
| 4,708,139 A | 11/1987 | Dunbar, IV |
| 4,713,077 A | 12/1987 | Small |
| 4,716,901 A | 1/1988 | Jackson et al. |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A * | 4/1988 | Sapega et al. ................. 606/96 |
| 4,741,330 A | 5/1988 | Hayhurst |
| 4,743,257 A | 5/1988 | Tormala |
| 4,749,585 A | 6/1988 | Greco et al. |
| 4,750,492 A | 6/1988 | Jacobs |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,781,182 A | 11/1988 | Purnell et al. |
| 4,790,303 A | 12/1988 | Steffee |
| 4,792,336 A | 12/1988 | Hlavacek et al. |
| 4,817,591 A | 4/1989 | Klaue |
| 4,822,224 A | 4/1989 | Carl et al. |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker et al. |
| 4,862,882 A | 9/1989 | Venturi et al. |
| 4,869,242 A | 9/1989 | Galluzzo |
| 4,870,957 A | 10/1989 | Goble et al. |
| 4,883,048 A | 11/1989 | Purnell et al. |

(56) References Cited

U.S. PATENT DOCUMENTS

| | | |
|---|---|---|
| 4,890,612 A | 1/1990 | Kensey |
| 4,895,148 A | 1/1990 | Bays et al. |
| 4,898,156 A | 2/1990 | Gatturna et al. |
| 4,899,729 A | 2/1990 | Gill et al. |
| 4,899,744 A | 2/1990 | Fujitsuka et al. |
| 4,901,721 A | 2/1990 | Hakki |
| 4,921,479 A | 5/1990 | Grayzel |
| 4,922,897 A * | 5/1990 | Sapega et al. .................. 606/80 |
| 4,924,866 A | 5/1990 | Yoon |
| 4,932,960 A | 6/1990 | Green et al. |
| 4,935,026 A | 6/1990 | McFadden |
| 4,935,028 A | 6/1990 | Drews |
| 4,945,625 A | 8/1990 | Winston |
| 4,946,468 A | 8/1990 | Li |
| 4,950,285 A | 8/1990 | Wilk |
| 4,954,126 A | 9/1990 | Wallsten |
| 4,955,910 A | 9/1990 | Bolesky |
| 4,957,498 A | 9/1990 | Caspari et al. |
| 4,961,741 A | 10/1990 | Hayhurst |
| 4,963,151 A | 10/1990 | Ducheyne et al. |
| 4,966,583 A | 10/1990 | Debbas |
| 4,968,315 A | 11/1990 | Gatturna |
| 4,968,317 A | 11/1990 | Tormala |
| 4,969,888 A | 11/1990 | Scholten et al. |
| 4,969,892 A | 11/1990 | Burton et al. |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka et al. |
| 5,009,652 A | 4/1991 | Morgan et al. |
| 5,009,663 A | 4/1991 | Broome |
| 5,009,664 A | 4/1991 | Sievers |
| 5,013,316 A | 5/1991 | Goble et al. |
| 5,019,090 A | 5/1991 | Pinchuk |
| 5,021,059 A | 6/1991 | Kensey et al. |
| 5,035,713 A | 7/1991 | Friis |
| 5,037,404 A | 8/1991 | Gold et al. |
| 5,037,422 A | 8/1991 | Hayhurst et al. |
| 5,041,093 A | 8/1991 | Chu |
| 5,041,114 A | 8/1991 | Chapman et al. |
| 5,041,129 A | 8/1991 | Hayhurst et al. |
| 5,046,513 A | 9/1991 | Gatturna et al. |
| 5,047,055 A | 9/1991 | Bao et al. |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,064,286 A | 11/1991 | Ai et al. |
| 5,069,674 A | 12/1991 | Fearnot et al. |
| 5,078,731 A | 1/1992 | Hayhurst |
| 5,078,744 A | 1/1992 | Chvapil |
| 5,078,745 A | 1/1992 | Rhenter et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante et al. |
| 5,100,405 A | 3/1992 | McLaren |
| 5,100,417 A | 3/1992 | Cerier et al. |
| 5,102,417 A | 4/1992 | Palmaz |
| 5,102,421 A | 4/1992 | Anspach, Jr. |
| 5,108,399 A | 4/1992 | Eitenmuller et al. |
| 5,120,175 A | 6/1992 | Arbegast et al. |
| 5,123,520 A | 6/1992 | Schmid |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,141,520 A | 8/1992 | Goble et al. |
| 5,147,362 A | 9/1992 | Goble |
| 5,154,720 A | 10/1992 | Trott et al. |
| 5,156,613 A | 10/1992 | Sawyer |
| 5,156,616 A | 10/1992 | Meadows et al. |
| 5,158,566 A | 10/1992 | Pianetti |
| 5,158,934 A | 10/1992 | Ammann et al. |
| 5,163,960 A | 11/1992 | Bonutti |
| 5,171,251 A | 12/1992 | Bregen et al. |
| 5,176,682 A | 1/1993 | Chow |
| 5,179,964 A | 1/1993 | Cook |
| 5,180,385 A | 1/1993 | Sontag |
| 5,180,388 A | 1/1993 | DiCarlo |
| 5,183,464 A | 2/1993 | Dubrul et al. |
| 5,192,287 A | 3/1993 | Fournier et al. |
| 5,192,326 A | 3/1993 | Bao et al. |
| 5,197,166 A | 3/1993 | Meier et al. |
| 5,197,971 A | 3/1993 | Bonutti |
| 5,203,784 A | 4/1993 | Ross et al. |
| 5,203,787 A | 4/1993 | Noblitt et al. |
| 5,208,950 A | 5/1993 | Merritt |
| 5,209,776 A | 5/1993 | Bass et al. |
| 5,217,493 A | 6/1993 | Raad et al. |
| 5,219,359 A | 6/1993 | McQuilkin et al. |
| 5,226,899 A | 7/1993 | Lee et al. |
| 5,234,006 A | 8/1993 | Eaton et al. |
| 5,234,425 A | 8/1993 | Fogarty et al. |
| 5,234,443 A * | 8/1993 | Phan et al. .................. 606/148 |
| 5,236,438 A | 8/1993 | Wilk |
| 5,236,445 A | 8/1993 | Hayhurst |
| 5,242,902 A | 9/1993 | Murphy |
| 5,254,113 A | 10/1993 | Wilk |
| 5,258,007 A | 11/1993 | Spetzler et al. |
| 5,258,015 A | 11/1993 | Li et al. |
| 5,258,016 A | 11/1993 | DiPoto et al. |
| 5,261,886 A | 11/1993 | Chesterfield |
| 5,266,325 A | 11/1993 | Kuzma et al. |
| 5,269,783 A | 12/1993 | Sander |
| 5,269,785 A | 12/1993 | Bonutti |
| 5,269,809 A | 12/1993 | Hayhurst et al. |
| 5,281,235 A | 1/1994 | Haber et al. |
| 5,282,832 A | 2/1994 | Toso et al. |
| 5,290,281 A | 3/1994 | Tschakaloff |
| 5,304,119 A | 4/1994 | Balaban et al. |
| 5,306,280 A | 4/1994 | Bregen et al. |
| 5,306,301 A | 4/1994 | Graf et al. |
| 5,315,741 A | 5/1994 | Dubberke |
| 5,318,588 A | 6/1994 | Horzewski et al. |
| 5,320,611 A | 6/1994 | Bonutti et al. |
| 5,324,308 A | 6/1994 | Pierce |
| 5,328,480 A | 7/1994 | Melker et al. |
| 5,329,846 A | 7/1994 | Bonutti |
| 5,329,924 A | 7/1994 | Bonutti |
| 5,330,468 A * | 7/1994 | Burkhart .................. 606/96 |
| 5,330,476 A | 7/1994 | Hiot et al. |
| 5,330,486 A | 7/1994 | Wilk |
| 5,336,231 A * | 8/1994 | Adair .................. 606/148 |
| 5,336,240 A | 8/1994 | Metzler et al. |
| 5,339,799 A | 8/1994 | Kami et al. |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,366,480 A | 11/1994 | Corriveau et al. |
| 5,370,646 A | 12/1994 | Reese et al. |
| 5,370,660 A | 12/1994 | Weinstein et al. |
| 5,372,146 A | 12/1994 | Branch |
| 5,374,235 A | 12/1994 | Ahrens |
| 5,376,126 A | 12/1994 | Lin |
| 5,382,254 A | 1/1995 | McGarry et al. |
| 5,383,883 A | 1/1995 | Wilk et al. |
| 5,383,905 A | 1/1995 | Golds et al. |
| 5,391,173 A | 2/1995 | Wilk |
| 5,395,308 A | 3/1995 | Fox et al. |
| 5,397,311 A | 3/1995 | Walker et al. |
| 5,400,805 A | 3/1995 | Warren |
| 5,403,312 A | 4/1995 | Yates et al. |
| 5,403,348 A | 4/1995 | Bonutti |
| 5,405,359 A | 4/1995 | Pierce |

(56) References Cited

U.S. PATENT DOCUMENTS

| | | |
|---|---|---|
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker et al. |
| 5,423,796 A | 6/1995 | Shikhman et al. |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr et al. |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock et al. |
| 5,453,090 A | 9/1995 | Martinez et al. |
| 5,456,722 A | 10/1995 | McLeod et al. |
| 5,458,653 A | 10/1995 | Davidson |
| 5,462,561 A | 10/1995 | Voda |
| 5,464,424 A | 11/1995 | O'Donnell, Jr. |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,478,351 A | 12/1995 | Meade et al. |
| 5,478,353 A | 12/1995 | Yoon |
| 5,480,403 A | 1/1996 | Lee et al. |
| 5,486,197 A | 1/1996 | Le et al. |
| 5,487,844 A | 1/1996 | Fujita |
| 5,488,958 A | 2/1996 | Topel et al. |
| 5,496,292 A | 3/1996 | Burnham |
| 5,496,318 A | 3/1996 | Howland |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,545,178 A | 8/1996 | Kensey et al. |
| 5,545,180 A | 8/1996 | Le et al. |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin et al. |
| 5,569,305 A | 10/1996 | Bonutti |
| 5,569,306 A | 10/1996 | Thal |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,578,046 A | 11/1996 | Liu |
| 5,580,344 A | 12/1996 | Hasson |
| 5,584,835 A | 12/1996 | Greenfield |
| 5,584,839 A * | 12/1996 | Gieringer ............... 606/96 |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van de Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,595 A | 2/1997 | Smith |
| 5,607,427 A | 3/1997 | Tschakaloff |
| 5,609,595 A | 3/1997 | Pennig |
| 5,618,314 A | 4/1997 | Harwin et al. |
| 5,620,461 A | 4/1997 | Muijs Van De Moer et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,634,926 A | 6/1997 | Jobe |
| 5,643,274 A | 7/1997 | Sander et al. |
| 5,643,293 A | 7/1997 | Kogasaka et al. |
| 5,643,295 A | 7/1997 | Yoon |
| 5,643,321 A | 7/1997 | McDevitt |
| 5,645,553 A | 7/1997 | Kolesa et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,665,089 A | 9/1997 | Dall et al. |
| 5,665,109 A | 9/1997 | Yoon |
| 5,667,513 A | 9/1997 | Torrie et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A * | 10/1997 | Burkhart et al. ............ 606/148 |
| 5,681,351 A | 10/1997 | Jamiolkowski et al. |
| 5,681,352 A | 10/1997 | Clancy, III et al. |
| 5,685,820 A | 11/1997 | Riek et al. |
| 5,688,283 A | 11/1997 | Knapp |
| 5,690,654 A | 11/1997 | Ovil |
| 5,690,655 A | 11/1997 | Hart et al. |
| 5,690,676 A | 11/1997 | DiPoto et al. |
| 5,693,055 A | 12/1997 | Zahiri et al. |
| 5,697,950 A | 12/1997 | Fucci et al. |
| 5,702,397 A | 12/1997 | Gonle et al. |
| 5,702,462 A | 12/1997 | Oberlander |
| 5,707,395 A | 1/1998 | Li |
| 5,713,903 A | 2/1998 | Sander et al. |
| 5,713,921 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,725,541 A | 3/1998 | Anspach, III et al. |
| 5,725,556 A | 3/1998 | Moser et al. |
| 5,725,582 A | 3/1998 | Bevan |
| 5,730,747 A | 3/1998 | Ek et al. |
| 5,733,306 A | 3/1998 | Bonutti |
| 5,735,875 A * | 4/1998 | Bonutti et al. ............. 606/232 |
| 5,735,877 A | 4/1998 | Pagedas |
| 5,735,899 A | 4/1998 | Schwartz et al. |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,766,221 A | 6/1998 | Benderev et al. |
| 5,769,894 A | 6/1998 | Ferragamo |
| 5,772,672 A | 6/1998 | Toy et al. |
| 5,776,151 A | 7/1998 | Chan |
| 5,779,706 A | 7/1998 | Tschakaloff |
| 5,782,862 A | 7/1998 | Bonutti |
| 5,785,713 A | 7/1998 | Jobe |
| 5,792,096 A | 8/1998 | Rentmeester et al. |
| 5,797,931 A | 8/1998 | Bito et al. |
| 5,800,537 A | 9/1998 | Bell |
| 5,807,403 A | 9/1998 | Beyar et al. |
| 5,810,849 A | 9/1998 | Kontos |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |

(56) References Cited

U.S. PATENT DOCUMENTS

| | | | |
|---|---|---|---|
| 5,823,994 A | 10/1998 | Sharkey et al. | |
| 5,824,009 A | 10/1998 | Fukuda et al. | |
| 5,830,125 A | 11/1998 | Scribner et al. | |
| 5,836,897 A | 11/1998 | Sakural et al. | |
| 5,839,899 A | 11/1998 | Robinson | |
| 5,843,084 A | 12/1998 | Hart | |
| 5,843,178 A | 12/1998 | Vanney et al. | |
| 5,845,645 A | 12/1998 | Bonutti | |
| 5,851,185 A | 12/1998 | Berns | |
| 5,865,834 A | 2/1999 | McGuire | |
| 5,866,634 A | 2/1999 | Tokushige | |
| 5,868,749 A | 2/1999 | Reed | |
| 5,874,235 A | 2/1999 | Chan | |
| 5,879,372 A | 3/1999 | Bartlett | |
| 5,891,166 A | 4/1999 | Schervinsky | |
| 5,891,168 A | 4/1999 | Thal | |
| 5,893,880 A | 4/1999 | Egan et al. | |
| 5,897,574 A | 4/1999 | Bonutti | |
| 5,899,911 A | 5/1999 | Carter | |
| 5,899,921 A | 5/1999 | Caspari et al. | |
| 5,906,579 A | 5/1999 | Vander Salm et al. | |
| 5,906,625 A | 5/1999 | Bito et al. | |
| 5,908,429 A | 6/1999 | Yoon | |
| 5,911,721 A | 6/1999 | Nicholson et al. | |
| 5,918,604 A | 7/1999 | Whelan | |
| 5,919,193 A | 7/1999 | Slavitt | |
| 5,919,194 A | 7/1999 | Anderson | |
| 5,919,208 A | 7/1999 | Valenti | |
| 5,919,215 A | 7/1999 | Wiklund et al. | |
| 5,921,986 A | 7/1999 | Bonutti | |
| 5,925,064 A | 7/1999 | Meyers et al. | |
| 5,928,244 A | 7/1999 | Tovey et al. | |
| 5,928,267 A | 7/1999 | Bonutti et al. | |
| 5,931,838 A | 8/1999 | Vito | |
| 5,931,869 A | 8/1999 | Boucher et al. | |
| 5,940,942 A | 8/1999 | Fong | |
| 5,941,900 A | 8/1999 | Bonutti | |
| 5,941,901 A | 8/1999 | Egan | |
| 5,944,750 A | 8/1999 | Tanner | |
| 5,945,002 A | 8/1999 | Leukes et al. | |
| 5,947,982 A | 9/1999 | Duran | |
| 5,948,000 A | 9/1999 | Larsen et al. | |
| 5,948,001 A | 9/1999 | Larsen | |
| 5,951,590 A | 9/1999 | Goldfarb | |
| 5,957,953 A | 9/1999 | DiPoto et al. | |
| 5,961,499 A | 10/1999 | Bonutti | |
| 5,961,521 A | 10/1999 | Roger | |
| 5,961,554 A | 10/1999 | Janson et al. | |
| 5,964,765 A | 10/1999 | Fenton, Jr. et al. | |
| 5,964,769 A | 10/1999 | Wagner et al. | |
| 5,968,046 A | 10/1999 | Castleman | |
| 5,968,047 A | 10/1999 | Reed | |
| 5,980,520 A | 11/1999 | Vancaillie | |
| 5,980,559 A | 11/1999 | Bonutti | |
| 5,984,929 A | 11/1999 | Bashiri et al. | |
| 5,989,282 A | 11/1999 | Bonutti | |
| 5,993,458 A * | 11/1999 | Vaitekunas et al. | 606/104 |
| 5,993,477 A | 11/1999 | Vaitekunas et al. | |
| 6,007,567 A | 12/1999 | Bonutti | |
| 6,007,580 A | 12/1999 | Lehto et al. | |
| 6,010,525 A | 1/2000 | Bonutti et al. | |
| 6,010,526 A | 1/2000 | Sandstrom et al. | |
| 6,017,321 A | 1/2000 | Boone | |
| 6,033,429 A | 3/2000 | Magovern | |
| 6,033,430 A | 3/2000 | Bonutti | |
| 6,045,551 A | 4/2000 | Bonutti | |
| 6,050,998 A | 4/2000 | Fletcher | |
| 6,056,751 A | 5/2000 | Fenton, Jr. | |
| 6,056,772 A | 5/2000 | Bonutti | |
| 6,056,773 A | 5/2000 | Bonutti | |
| 6,059,797 A * | 5/2000 | Mears | 606/140 |
| 6,059,817 A | 5/2000 | Bonutti et al. | |
| 6,059,827 A | 5/2000 | Fenton | |
| 6,063,095 A | 5/2000 | Wang et al. | |
| 6,066,151 A | 5/2000 | Miyawaki et al. | |
| 6,066,160 A | 5/2000 | Colvin et al. | |
| 6,066,166 A | 5/2000 | Bischoff et al. | |
| 6,068,637 A | 5/2000 | Popov et al. | |
| 6,068,648 A | 5/2000 | Cole | |
| 6,077,277 A * | 6/2000 | Mollenauer et al. | 606/144 |
| 6,077,292 A | 6/2000 | Bonutti | |
| 6,080,161 A | 6/2000 | Eaves, III et al. | |
| 6,083,522 A | 7/2000 | Chu et al. | |
| 6,086,593 A | 7/2000 | Bonutti | |
| 6,086,608 A | 7/2000 | Ek et al. | |
| 6,090,072 A | 7/2000 | Kratoska et al. | |
| 6,099,531 A | 8/2000 | Bonutti | |
| 6,099,537 A | 8/2000 | Sugai et al. | |
| 6,099,550 A | 8/2000 | Yoon | |
| 6,099,552 A | 8/2000 | Adams | |
| 6,102,850 A | 8/2000 | Wang et al. | |
| 6,106,545 A | 8/2000 | Egan | |
| 6,117,160 A | 9/2000 | Bonutti | |
| 6,120,511 A * | 9/2000 | Chan | A61B 17/1637 606/102 |
| 6,120,536 A | 9/2000 | Ding et al. | |
| 6,125,574 A | 10/2000 | Ganaja et al. | |
| 6,126,677 A | 10/2000 | Ganaja et al. | |
| 6,139,320 A | 10/2000 | Hahn | |
| RE36,974 E | 11/2000 | Bonutti | |
| 6,149,669 A | 11/2000 | Li | |
| 6,152,949 A | 11/2000 | Bonutti | |
| 6,155,756 A | 12/2000 | Mericle et al. | |
| 6,159,224 A | 12/2000 | Yoon | |
| 6,159,234 A | 12/2000 | Bonutti et al. | |
| 6,171,299 B1 | 1/2001 | Bonutti | |
| 6,171,307 B1 | 1/2001 | Orlich | |
| 6,174,324 B1 * | 1/2001 | Egan et al. | 606/232 |
| 6,179,840 B1 | 1/2001 | Bowman | |
| 6,179,850 B1 | 1/2001 | Goradia | |
| 6,187,008 B1 | 2/2001 | Hamman | |
| 6,190,400 B1 | 2/2001 | Van De Moer et al. | |
| 6,190,401 B1 | 2/2001 | Green | |
| 6,200,322 B1 | 3/2001 | Branch et al. | |
| 6,217,591 B1 | 4/2001 | Egan et al. | |
| 6,224,593 B1 | 5/2001 | Ryan | |
| 6,224,630 B1 | 5/2001 | Bao et al. | |
| 6,228,086 B1 | 5/2001 | Wahl et al. | |
| 6,231,592 B1 | 5/2001 | Bonutti et al. | |
| 6,238,395 B1 | 5/2001 | Bonutti | |
| 6,238,396 B1 | 5/2001 | Lombardo | |
| 6,258,091 B1 | 7/2001 | Sevrain et al. | |
| 6,264,675 B1 | 7/2001 | Brotz | |
| 6,267,761 B1 | 7/2001 | Ryan | |
| 6,273,717 B1 | 8/2001 | Hahn et al. | |
| 6,280,474 B1 | 8/2001 | Cassidy et al. | |
| 6,286,746 B1 | 9/2001 | Egan et al. | |
| 6,287,325 B1 | 9/2001 | Bonutti | |
| 6,293,961 B2 | 9/2001 | Schwartz et al. | |
| 6,306,159 B1 | 10/2001 | Schwartz et al. | |
| 6,309,405 B1 | 10/2001 | Bonutti | |
| 6,312,448 B1 | 11/2001 | Bonutti | |
| 6,338,730 B1 | 1/2002 | Bonutti et al. | |
| 6,340,365 B2 | 1/2002 | Dittrich et al. | |
| 6,348,056 B1 | 2/2002 | Bates et al. | |
| 6,358,271 B1 | 3/2002 | Egan et al. | |
| 6,364,897 B1 | 4/2002 | Bonutti | |
| 6,368,325 B1 | 4/2002 | McKinley et al. | |
| 6,368,343 B1 | 4/2002 | Bonutti et al. | |
| 6,371,957 B1 | 4/2002 | Amrein et al. | |
| 6,409,742 B1 | 6/2002 | Fulton, III | |
| 6,409,743 B1 | 6/2002 | Fenton, Jr. | |
| 6,419,704 B1 | 7/2002 | Ferree | |
| 6,423,088 B1 | 7/2002 | Fenton | |
| 6,425,919 B1 | 7/2002 | Lambrecht | |
| 6,428,562 B2 | 8/2002 | Bonutti | |
| 6,432,115 B1 | 8/2002 | Mollenauer et al. | |
| 6,447,516 B1 | 9/2002 | Bonutti | |
| 6,450,985 B1 | 9/2002 | Schoelling et al. | |
| 6,461,360 B1 | 10/2002 | Adam | |
| 6,468,293 B2 | 10/2002 | Bonutti et al. | |
| 6,475,230 B1 | 11/2002 | Bonutti | |
| 6,488,196 B1 | 12/2002 | Fenton | |
| 6,500,195 B2 | 12/2002 | Bonutti | |

(56) References Cited

U.S. PATENT DOCUMENTS

| | | |
|---|---|---|
| 6,503,259 B2 | 1/2003 | Huxel et al. |
| 6,527,774 B2 | 3/2003 | Lieberman |
| 6,530,933 B1 | 3/2003 | Yeung et al. |
| 6,535,764 B2 | 3/2003 | Imran et al. |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,551,343 B1 | 4/2003 | Tormala |
| 6,554,852 B1 | 4/2003 | Oberlander |
| 6,557,426 B2 | 5/2003 | Reinemann et al. |
| 6,558,390 B2 | 5/2003 | Cragg |
| 6,568,313 B2 | 5/2003 | Fukui et al. |
| 6,569,187 B1 | 5/2003 | Bonutti |
| 6,572,635 B1 | 6/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,592,609 B1 | 7/2003 | Bonutti |
| 6,594,517 B1 | 7/2003 | Nevo |
| 6,602,293 B1 | 8/2003 | Biermann |
| 6,605,090 B1 | 8/2003 | Trieu et al. |
| 6,610,080 B2 | 8/2003 | Morgan |
| 6,618,910 B1 | 9/2003 | Pontaoe |
| 6,623,486 B1 | 9/2003 | Weaver |
| 6,623,487 B1 | 9/2003 | Goshert |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer et al. |
| 6,645,227 B2 | 11/2003 | Fallin et al. |
| 6,666,877 B2 | 12/2003 | Morgan et al. |
| 6,669,705 B2 | 12/2003 | Westhaver et al. |
| 6,679,888 B2 * | 1/2004 | Green et al. ............. 606/86 R |
| 6,685,750 B1 | 2/2004 | Plos et al. |
| 6,699,240 B2 | 3/2004 | Francischelli |
| 6,702,821 B2 | 3/2004 | Bonutti |
| 6,705,179 B1 | 3/2004 | Mohtasham |
| 6,709,457 B1 | 3/2004 | Otte |
| 6,719,765 B2 | 4/2004 | Bonutti |
| 6,719,795 B1 | 4/2004 | Cornwall |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li et al. |
| 6,770,078 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |
| 6,818,010 B2 | 11/2004 | Eichhorn et al. |
| 6,823,871 B2 | 11/2004 | Schmieding |
| 6,830,589 B2 | 12/2004 | Erickson |
| 6,860,885 B2 | 3/2005 | Bonutti |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,128,763 B1 | 10/2006 | Blatt |
| 7,147,652 B2 | 12/2006 | Bonutti et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,326,200 B2 | 2/2008 | Trieu |
| 7,329,263 B2 | 2/2008 | Bonutti |
| 7,335,205 B2 | 2/2008 | Aeschlimann |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 | 3/2009 | Raterman |
| 7,597,705 B2 | 10/2009 | Forsberg |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 8,771,314 B2 | 7/2014 | Crombie |
| 8,845,699 B2 | 9/2014 | Bonutti |
| 2001/0002440 A1 | 5/2001 | Bonutti |
| 2001/0008971 A1 | 7/2001 | Schwartz |
| 2001/0009250 A1 | 7/2001 | Herman et al. |
| 2001/0041916 A1 | 11/2001 | Bonutti |
| 2001/0056287 A1 | 12/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029067 A1 | 3/2002 | Bonutti |
| 2002/0029083 A1 | 3/2002 | Zucherman et al. |
| 2002/0029084 A1 | 3/2002 | Paul et al. |
| 2002/0045902 A1 | 4/2002 | Bonutti |
| 2002/0058966 A1 | 5/2002 | Tormala |
| 2002/0062153 A1 | 5/2002 | Paul et al. |
| 2002/0087189 A1 | 7/2002 | Bonutti |
| 2002/0103495 A1 | 8/2002 | Cole |
| 2002/0120269 A1 | 8/2002 | Lange |
| 2002/0123750 A1 | 9/2002 | Eisermann et al. |
| 2002/0161439 A1 | 10/2002 | Strobel |
| 2002/0183762 A1 | 12/2002 | Anderson et al. |
| 2002/0188301 A1 * | 12/2002 | Dallara et al. ............ 606/104 |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0083667 A1 * | 5/2003 | Ralph et al. ............... 606/96 |
| 2003/0097148 A1 | 5/2003 | Valimaa |
| 2003/0105474 A1 | 6/2003 | Bonutti |
| 2003/0118518 A1 | 6/2003 | Hahn et al. |
| 2003/0125749 A1 | 7/2003 | Yuan |
| 2003/0158555 A1 | 8/2003 | Sanders |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0195514 A1 | 10/2003 | Trieu |
| 2003/0195530 A1 | 10/2003 | Thill |
| 2003/0195565 A1 | 10/2003 | Bonutti |
| 2003/0204204 A1 | 10/2003 | Bonutti |
| 2003/0208203 A1 | 11/2003 | Lim |
| 2003/0216742 A1 | 11/2003 | Wetzler et al. |
| 2003/0225438 A1 | 12/2003 | Bonutti et al. |
| 2003/0229361 A1 | 12/2003 | Jackson |
| 2004/0010287 A1 | 1/2004 | Bonutti |

(56) References Cited

U.S. PATENT DOCUMENTS

| | | |
|---|---|---|
| 2004/0024459 A1 | 2/2004 | Ferree |
| 2004/0030341 A1 | 2/2004 | Aeschlimann et al. |
| 2004/0034357 A1 | 2/2004 | Beane et al. |
| 2004/0039392 A1 | 2/2004 | Trieu |
| 2004/0049207 A1 | 3/2004 | Goldfarb |
| 2004/0097939 A1 | 5/2004 | Bonutti |
| 2004/0098050 A1 | 5/2004 | Foerster et al. |
| 2004/0102788 A1* | 5/2004 | Huebner et al. ............ 606/96 |
| 2004/0116963 A1 | 6/2004 | Lattouf |
| 2004/0138703 A1 | 7/2004 | Alleyne |
| 2004/0138705 A1 | 7/2004 | Heino |
| 2004/0143334 A1 | 7/2004 | Ferree |
| 2004/0167548 A1 | 8/2004 | Bonutti |
| 2004/0172063 A1 | 9/2004 | Li |
| 2004/0186471 A1 | 9/2004 | Trieu |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti et al. |
| 2005/0033362 A1 | 2/2005 | Grafton |
| 2005/0033366 A1 | 2/2005 | Cole |
| 2005/0038514 A1 | 2/2005 | Helm et al. |
| 2005/0043733 A1 | 2/2005 | Eisermann |
| 2005/0043796 A1 | 2/2005 | Grant et al. |
| 2005/0070765 A1 | 3/2005 | Abdelgany |
| 2005/0071012 A1 | 3/2005 | Serhan et al. |
| 2005/0075644 A1 | 4/2005 | DiPoto |
| 2005/0090827 A1 | 4/2005 | Gedebou |
| 2005/0096699 A1 | 5/2005 | Wixey et al. |
| 2005/0113928 A1 | 5/2005 | Cragg et al. |
| 2005/0125072 A1 | 6/2005 | Kolb |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0234460 A1 | 10/2005 | Miller |
| 2005/0240190 A1 | 10/2005 | Gall |
| 2005/0240227 A1 | 10/2005 | Bonutti |
| 2005/0246021 A1 | 11/2005 | Ringeisen et al. |
| 2005/0256582 A1 | 11/2005 | Ferree |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2005/0283246 A1 | 12/2005 | Cauthen |
| 2006/0009846 A1 | 1/2006 | Trieu |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0064095 A1 | 3/2006 | Senn et al. |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0142799 A1 | 6/2006 | Bonutti |
| 2006/0167495 A1 | 7/2006 | Bonutti |
| 2006/0189982 A1 | 8/2006 | Lange |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0235413 A1 | 10/2006 | Denham |
| 2006/0235470 A1 | 10/2006 | Bonutti |
| 2006/0241695 A1 | 10/2006 | Bonutti |
| 2006/0264953 A1 | 11/2006 | Falahee |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0088362 A1 | 4/2007 | Bonutti et al. |
| 2007/0118129 A1 | 5/2007 | Fraser et al. |
| 2007/0198555 A1 | 8/2007 | Friedman et al. |
| 2007/0233092 A1 | 10/2007 | Falahee |
| 2007/0265561 A1 | 11/2007 | Yeung |
| 2007/0270833 A1 | 11/2007 | Bonutti |
| 2008/0021474 A1 | 1/2008 | Bonutti et al. |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0097448 A1 | 4/2008 | Binder et al. |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0195145 A1 | 8/2008 | Bonutti |
| 2008/0269753 A1 | 10/2008 | Cannestra |
| 2008/0269808 A1 | 10/2008 | Gall et al. |
| 2009/0024161 A1 | 1/2009 | Bonutti |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti |
| 2011/0060375 A1 | 3/2011 | Bonutti |
| 2011/0295253 A1 | 12/2011 | Bonutti et al. |
| 2012/0165841 A1 | 6/2012 | Bonutti |
| 2012/0191140 A1 | 7/2012 | Bonutti |
| 2012/0215233 A1 | 8/2012 | Bonutti et al. |

FOREIGN PATENT DOCUMENTS

| | | |
|---|---|---|
| CA | 2698057 | 3/2009 |
| DE | 1903016 | 8/1970 |
| DE | 3517204 | 11/1986 |
| DE | 3722538 | 1/1989 |
| DE | 9002844 | 12/1990 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 91/12779 | 9/1991 |
| WO | 9408642 | 4/1994 |
| WO | WO 95/31941 | 11/1995 |
| WO | 9614802 | 5/1996 |
| WO | 9712779 | 4/1997 |
| WO | 97/49347 | 12/1997 |
| WO | WO 97/49347 | 12/1997 |
| WO | 9811838 | 3/1998 |
| WO | 9826720 | 6/1998 |
| WO | 02053011 | 7/2002 |
| WO | 2007/092869 | 8/2007 |
| WO | 2007/092869 A2 | 8/2007 |
| WO | 2008/116203 | 9/2008 |
| WO | 2009/029908 | 3/2009 |
| WO | 2009124215 | 10/2009 |
| WO | 2010099222 | 2/2010 |

OTHER PUBLICATIONS

Copending U.S. Appl. No. 11/456,132, Non-Final Rejection mailed Jun. 18, 2007.
Copending U.S. Appl. No. 11/456,132, Response to Office Action Nov. 19, 2007.
Copending U.S. Appl. No. 11/456,132, Final Rejection mailed Mar. 11, 2008.
Copending U.S. Appl. No. 11/456,132, Request for Continued Examination Jun. 11, 2008.

(56) References Cited

OTHER PUBLICATIONS

Copending U.S. Appl. No. 11/456,132, Response to Office Action Jun. 11, 2008.
Copending U.S. Appl. No. 11/456,132, Non-Final Rejection mailed Oct. 7, 2008.
Copending U.S. Appl. No. 11/456,132, Response to Office Action Jan. 7, 2009.
Copending U.S. Appl. No. 11/456,132, Non-Final Rejection mailed Mar. 13, 2009.
Copending U.S. Appl. No. 11/456,132, Response to Office Action Aug. 13, 2009.
Copending U.S. Appl. No. 11/456,132, Examiner Interview Summary mailed Aug. 28, 2009.
Copending U.S. Appl. No. 11/456,132, Final Rejection mailed Dec. 18, 2009.
Copending U.S. Appl. No. 11/456,132, Response to Office Action Apr. 19, 2010.
Copending U.S. Appl. No. 11/456,221, filed Jul. 10, 2006.
Copending U.S. Appl. No. 11/456,221, Non-Final Rejection mailed Jul. 9, 2007.
Copending U.S. Appl. No. 11/456,221, Response to Office Action Nov. 9, 2007.
Copending U.S. Appl. No. 11/456,221, Final Rejection mailed Feb. 22, 2008.
Copending U.S. Appl. No. 11/456,221, Response to Office Action May 22, 2008.
Copending U.S. Appl. No. 11/456,221, Request for Continued Examintation Jun. 19, 2008.
Copending U.S. Appl. No. 11/456,221, Non-Final Rejection mailed Oct. 29, 2008.
Copending U.S. Appl. No. 11/456,221, Response to Office Action Mar. 30, 2009.
Copending U.S. Appl. No. 11/456,221, Non-Final Rejection mailed Jul. 6, 2009.
Copending U.S. Appl. No. 11/456,221, Response to Office Action Jan. 6, 2010.
Copending U.S. Appl. No. 11/456,221, Final Rejection mailed Mar. 24, 2010.
Copending U.S. Appl. No. 11/932,051, filed Oct. 31, 2007.
Copending U.S. Appl. No. 11/932,051, Requirement for Restriction Jan. 22, 2010.
Copending U.S. Appl. No. 10/228,855, filed Aug. 27, 2002.
Copending U.S. Appl. No. 10/228,855, Non-Final Rejection mailed Sep. 28, 2005.
Copending U.S. Appl. No. 10/228,855, Response to Office Action Dec. 28, 2005.
Copending U.S. Appl. No. 11/465,199, filed Aug. 17, 2006.
Copending U.S. Appl. No. 11/465,199, Non-Final Rejecrion mailed Dec. 28, 2009.
Copending U.S. Appl. No. 11/932,602, filed Oct. 31, 2007.
Copending U.S. Appl. No. 10/780,444, filed Feb. 17, 2004.
Copending U.S. Appl. No. 10/780,444, Requirement for Restriction Apr. 10, 2007.
Copending U.S. Appl. No. 10/780,444, Response to Office Action May 10, 2007.
Copending U.S. Appl. No. 10/780,444, Requirement for Restriction Sep. 12, 2007.
Copending U.S. Appl. No. 10/780,444, Response to Office Action Oct. 12, 2007.
Copending U.S. Appl. No. 10/780,444, Non-Final Rejection mailed Mar. 11, 2008.
Copending U.S. Appl. No. 10/780,444, Response to Office Action Jul. 9, 2008.
Copending U.S. Appl. No. 10/780,444, Final Rejection mailed Dec. 23, 2008.
Copending U.S. Appl. No. 10/780,444, Response to Office Action Apr. 23, 2009.
Copending U.S. Appl. No. 10/780,444, Request for Continued Examination Apr. 23, 2009.
Copending U.S. Appl. No. 10/780,444, Non-Final Rejection mailed Jul. 7, 2009.
Copending U.S. Appl. No. 10/780,444, Examiner Interview Summary mailed Nov. 20, 2009.
Copending U.S. Appl. No. 10/780,444, Response to Office Action Dec. 4, 2009.
Copending U.S. Appl. No. 10/780,444, Final Rejection mailed Mar. 30, 2010.
Copending U.S. Appl. No. 10/779,978, filed Feb. 17, 2004.
Copending U.S. Appl. No. 10/779,978, Requirement for Restriction Apr. 20, 2007.
Copending U.S. Appl. No. 10/779,978, Response to Office Action May 21, 2007.
Copending U.S. Appl. No. 10/779,978, Non-Final Rejection mailed Aug. 3, 2007.
Copending U.S. Appl. No. 09/556,458.
Copending U.S. Appl. No. 09/556,458, Non-Final Rejection mailed Sep. 25, 2002.
Copending U.S. Appl. No. 09/556,458, Response to Office Action Dec. 26, 2002.
Copending U.S. Appl. No. 10/614,352, filed Jul. 7, 2003.
Copending U.S. Appl. No. 10/614,352, Non-Final Rejection mailed Dec. 1, 2005.
Copending U.S. Appl. No. 10/614,352, Response to Office Action Mar. 1, 2006.
Copending U.S. Appl. No. 10/614,352, Non-Final Rejection mailed Aug. 1, 2006.
Copending U.S. Appl. No. 10/614,352, Response to Office Action Nov. 1, 2006.
Copending U.S. Appl. No. 10/614,352, Final Rejection mailed Jan. 25, 2007.
Copending U.S. Appl. No. 10/614,352, Response to Office Action Mar. 26, 2007.
Copending U.S. Appl. No. 10/614,352, Non-Final Rejection mailed Apr. 17, 2007.
Copending U.S. Appl. No. 10/614,352, Response to Office Action Jul. 17, 2007.
Copending U.S. Appl. No. 10/614,352, Examiner Interview Summary Jul. 31, 2007.
Copending U.S. Appl. No. 10/614,352, Final Rejection mailed Oct. 2, 2007.
Copending U.S. Appl. No. 10/614,352, Request for Continued Examination Oct. 30, 2007.
Copending U.S. Appl. No. 10/614,352, Response to Office Action Oct. 30, 2007.
Copending U.S. Appl. No. 10/614,352, Non-Final Rejection mailed Jan. 15, 2008.
Copending U.S. Appl. No. 10/614,352, Response to Office Action May 15, 2008.
Copending U.S. Appl. No. 10/614,352, Non-Final Rejection mailed Aug. 21, 2008.
Copending U.S. Appl. No. 10/614,352, Response to Office Action Dec. 22, 2008.
Copending U.S. Appl. No. 10/614,352, Final Rejection mailed Apr. 14, 2009.
Copending U.S. Appl. No. 10/614,352, Request for Continued Examination Sep. 14, 2009.
Copending U.S. Appl. No. 10/614,352, Response to Office Action Sep. 14, 2009.
Copending U.S. Appl. No. 10/614,352, Non-Final Rejection mailed Nov. 24, 2009.
Copending U.S. Appl. No. 10/614,352, Response to Office Action Apr. 26, 2010.
Copending U.S. Appl. No. 11/931,823, filed Oct. 31, 2007.
Copending U.S. Appl. No. 09/789,621, filed Feb. 21, 2001.
Copending U.S. Appl. No. 10/413,696, filed Apr. 14, 2033.
Copending U.S. Appl. No. 10/413,696, Requirement for Restriction Jun. 8, 2005.
Copending U.S. Appl. No. 10/413,696, Response to Office Action Jul. 5, 2005.
Copending U.S. Appl. No. 10/413,696, Non-Final Rejection mailed Sep. 23, 2005.

(56) References Cited

OTHER PUBLICATIONS

Copending U.S. Appl. No. 10/413,696, Response to Office Action Dec. 20, 2005.
Copending U.S. Appl. No. 11/460,650, filed Jul. 28, 2006.
Copending U.S. Appl. No. 11/460,650, Non-Final Rejection mailed May 30, 2007.
Copending U.S. Appl. No. 11/460,650, Response to Office Action Oct. 1, 2007.
Copending U.S. Appl. No. 11/460,650, Non-Final Rejection mailed Dec. 28, 2007.
Copending U.S. Appl. No. 11/460,650, Response to Office Action Mar. 28, 2008.
Copending U.S. Appl. No. 11/460,650, Final Rejection mailed Aug. 29, 2008.
Copending U.S. Appl. No. 11/460,650, Request for Continued Examination Jan. 29, 2009.
Copending U.S. Appl. No. 11/460,650, Response to Office Action Jan. 29, 2009.
Copending U.S. Appl. No. 11/460,650, Non-Final Rejection mailed Mar. 10, 2009.
Copending U.S. Appl. No. 11/460,650, Response to Office Action Jun. 10, 2009.
Copending U.S. Appl. No. 11/460,650, Non-Final Rejection mailed Sep. 16, 2009.
Copending U.S. Appl. No. 11/460,650, Examiner Interview Summary mailed Dec. 23, 2009.
Copending U.S. Appl. No. 11/460,650, Response to Office Action Jan. 12, 2010.
Copending U.S. Appl. No. 11/460,650, Final Rejection mailed Apr. 20, 2010.
Copending U.S. Appl. No. 11/461,110, filed Jul. 31, 2006.
Copending U.S. Appl. No. 11/461,110, Non-Final Rejection mailed May 14, 2007.
Copending U.S. Appl. No. 11/461,110, Response to Office Action Oct. 15, 2007.
Copending U.S. Appl. No. 11/461,110, Final Rejection mailed Dec. 12, 2007.
Copending U.S. Appl. No. 11/187,482 Response to Office Action Jun. 21, 2011.
Copending U.S. Appl. No. 12/359,364, Final Office Action Apr. 7, 2011.
Copending U.S. Appl. No. 11/932,907, Response to Office Action Apr. 18, 2011.
Copending U.S. Appl. No. 11/932,907, non-final Office Action Nov. 17, 2010.
Copending U.S. Appl. No. 11/133,730 Final Office action Aug. 17, 2011.
Copending U.S. Appl. No. 11/169,475 Office Action.
Copending U.S. Appl. No. 11/169,475—Response Sep. 2, 2011.
Copending U.S. Appl. No. 11/932,051, RCE Response Dec. 9, 2011.
Copending U.S. Appl. No. 11/456,132, Response to Office Action Jan. 18, 2012.
Copending U.S. Appl. No. 11/202,294, Office Action mailed Jun. 24, 2011.
Copending U.S. Appl. No. 11/202,294, Response filed Dec. 24, 2011.
Copending U.S. Appl. No. 12/202,210, Requirement for Restriction mailed Aug. 16, 2011.
Copending U.S. Appl. No. 12/202,210, Response filed Dec. 16, 2011.
Copending U.S. Appl. No. 11/456,132, Response filed Jan. 18, 2012.
Copending U.S. Appl. No. 10/780,444, Response filed Feb. 9, 2012.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO/2009/029908, published May 3, 2009 for PCTUS2008/074941.
ISR—International Search Report, WO /2009/029908, published May 3, 2009 for PCTUS2008/074941.
IPER—Internation Preliminary Report on Patentability, WO/2009/029908, published Mar. 2, 2010 for PCTUS2008/074941.
Written Opinion WO/2009/029908 dated Feb. 28, 2010 for PCTUS2008/074941.
Canadian Patent Application #2680827 equivalent to U.S. Appl. No. 11/689,670, P. Bonutti, Sep. 22, 2009.
ISR—International Search Report PCT/US2010/025263 completed Apr. 13, 2010.
Written Opinion for PCT/US2010/025263 completed Apr. 13, 2010.
Copending U.S. Appl. No. 11/461,110, Request for Continued Examination Jun. 8, 2010.
Copending U.S. Appl. No. 11/461,110, Response to Office Action Jun. 8, 2010.
Copending U.S. Appl. No. 11/930,621, Final Rejection Jun. 22, 2010.
Copending U.S. Appl. No. 11/465,199, Response to Office Action Jun. 28, 2010.
Copending U.S. Appl. No. 12/711,540, filed Feb. 24, 2010.
Copending U.S. Appl. No. 11/931,823 RestrictionElect dated Jun. 8, 2010.
Copending U.S. Appl. No. 11/931,823 Response to Office Action Aug. 9, 2010.
Copending U.S. Appl. No. 11/931,823 Office Action mailed Nov. 24, 2010.
Copending U.S. Appl. No. 11/416,618, Request for Continued Examination Dec. 8, 2011.
Copending U.S. Appl. No. 11/689,670, Response to Office Action Jan. 3, 2011.
Copending U.S. Appl. No. 11/370,775, Request for Continued Examination Jan. 10, 2011.
Copending U.S. Appl. No. 10/779,978 Non-Final Office Action mailed Jan. 13, 2011.
Copending U.S. Appl. No. 11/671,556 Final Office Action mailed Nov. 12, 2010.
Copending U.S. Appl. No. 11/689,670, Final Office Action mailed Mar. 17, 2011.
Copending U.S. Appl. No. 11/932,602 non final Office Action Oct. 6, 2010.
Copending U.S. Appl. No. 11/456,132, Response to Office Action Apr. 14, 2011.
Copending U.S. Appl. No. 11/932,602, Response to Office Action Apr. 6, 2011.
Copending U.S. Appl. No. 11/874,323 Response filed Apr. 21, 2011.
Copending U.S. Appl. No. 11/932,051 Final Office Action mailed Jun. 9, 2011.
Copending U.S. Appl. No. 11/358,399 Response filed Jul. 5, 2011.
Copending U.S. Appl. No. 10/779,978, Response to Office Action Jul. 13, 2011.
Copending U.S. Appl. No. 11/358,399 non Final Office Action Jan. 3, 2011.
Copending U.S. Appl. No. 11/874,323 Office Action mailed Jul. 6, 2011.
Copending U.S. Appl. No. 10/780,444, nonFinal Office Action Aug. 9, 2011.
Copending U.S. Appl. No. 10/614,352, non Final Office Action Aug. 10, 2011.
Copending U.S. Appl. No. 11/931,823 final Office Action mailed Aug. 2, 2011.
Copending U.S. Appl. No. 11/265,432 non Final OfficeAction Aug. 10, 2011.
Copending U.S. Appl. No. 11/438,537—RCE Response filed Nov. 21, 2011.
Copending U.S. Appl. No. 10/779,978, Response to Office Action Dec. 3, 2007.
Copending U.S. Appl. No. 10/779,978, Response to Office Action Mar. 25, 2008.

(56) References Cited

OTHER PUBLICATIONS

Copending U.S. Appl. No. 10/779,978, Non-Final Rejection mailed Jun. 18, 2008.
Copending U.S. Appl. No. 10/779,978, Response to Office Action Oct. 20, 2008.
Copending U.S. Appl. No. 10/779,978, Final Rejection mailed Feb. 3, 2009.
Copending U.S. Appl. No. 10/779,978, Request for Continued Examination Jul. 6, 2009.
Copending U.S. Appl. No. 10/779,978, Response to Office Action Jul. 6, 2009.
Copending U.S. Appl. No. 10/779,978, Non-Final Rejection mailed Oct. 1, 2009.
Copending U.S. Appl. No. 10/779,978, Response to Office Action Feb. 1, 2010.
Copending U.S. Appl. No. 10/779,978, Final Rejection mailed May 14, 2010.
Copending U.S. Appl. No. 10/797,685, filed Mar. 9, 2004.
Copending U.S. Appl. No. 10/797,685, Non-Final Rejection mailed Nov. 17, 2006.
Copending U.S. Appl. No. 10/797,685, Response to Office Action Feb. 20, 2007.
Copending U.S. Appl. No. 10/797,685, Final Rejection mailed Apr. 25, 2007.
Copending U.S. Appl. No. 10/797,685, Response to Office Action Aug. 27, 2007.
Copending U.S. Appl. No. 10/797,685, Examiner Interview Summary mailed Sep. 11, 2007.
Copending U.S. Appl. No. 11/874,323, filed Oct. 18, 2007.
Copending U.S. Appl. No. 11/671,556, filed Feb. 6, 2007.
Copending U.S. Appl. No. 11/671,556, Requirement for Restriction Sep. 1, 2009.
Copending U.S. Appl. No. 11/671,556, Response to Office Action Nov. 2, 2009.
Copending U.S. Appl. No. 11/671,556, Non-Final Rejection mailed Feb. 22, 2010.
Copending U.S. Appl. No. 11/416,618, filed May 3, 2006.
Copending U.S. Appl. No. 11/416,618, Non-Final Rejection mailed Nov. 26, 2008.
Copending U.S. Appl. No. 11/416,618, Response to Office Action Mar. 26, 2009.
Copending U.S. Appl. No. 11/416,618, Final Rejection mailed Jun. 24, 2009.
Copending U.S. Appl. No. 11/416,618, Response to Office Action Sep. 24, 2009.
Copending U.S. Appl. No. 11/416,618, Non-Final Rejection mailed Oct. 13, 2009.
Copending U.S. Appl. No. 11/416,618, Response to Office Action Mar. 15, 2010.
Copending U.S. Appl. No. 11/416,618, Examiner Interview Summary mailed Apr. 15, 2010.
Copending U.S. Appl. No. 11/416,618, Response to Office Action Apr. 16, 2010.
Copending U.S. Appl. No. 11/689,670, filed Mar. 22, 2007.
Copending U.S. Appl. No. 11/689,670, Requirement for Restriction Mar. 15, 2010.
Copending U.S. Appl. No. 11/689,670, Response to Office Action Apr. 15, 2010.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arcioscopic and Related Surgery, 1994.
Problem Solving Report Question No. 1014984.066, Ultrasonic Welding, (c) 1999.
Guide to Ultrasound Plastic Assembly, Ultrasonic Division Publication, (c) 1995.
Enabling Local Drug Delivery—Implant Device Combination Therapies, Surmodics, Inc., (c) 2003.
Why Tie a Knot When You Can Use Y-Knot?, Innovasive Devices Inc., (c) 1998.
Ask Oxford projection, compact oxford english dicitionary: projection, Mar. 30, 2009.
Ask Oxford projection, compact oxford english dicitionary: slit, Mar. 30, 2009.
Textured Surface Technology, Branson Technolog, Branson Ultrasonics Copr., (c) 1992.
IPR—International Publication WO/2007/092869, publishedAug. 16, 2007 for PCT/US2007/061730.
ISR—International Search Report WO/2007/092869, published Dec. 13, 2007 for PCT/US2007/061730.
IPER—Internation Preliminary Report on Patentability, WO/2007/092869, published Aug. 12, 2008 for PCT/US2007/061730.
Written Opinion WO/2007/092869 dated Aug. 7, 2008 for PCT/US2007/061730.
Copending U.S. Appl. No. 11/461,110, Request for Continued Examination Mar. 12, 2008.
Copending U.S. Appl. No. 11/461,110, Response to Office Action Mar. 12, 2008.
Copending U.S. Appl. No. 11/461,110, Non-Final Rejection mailed Jun. 6, 2008.
Copending U.S. Appl. No. 11/461,110, Response to Office Action Oct. 6, 2008.
Copending U.S. Appl. No. 11/461,110, Non-Final Rejection mailed Apr. 22, 2009.
Copending U.S. Appl. No. 11/461,110, Response to Office Action Sep. 22, 2009.
Copending U.S. Appl. No. 11/461,110, Final Rejection mailed Dec. 8, 2009.
Copending U.S. Appl. No. 11/930,621, filed Oct. 31, 2007.
Copending U.S. Appl. No. 11/930,621, Non-Final Rejection mailed Sep. 21, 2009.
Copending U.S. Appl. No. 11/930,621, Response to Office Action Mar. 22, 2010.
Copending U.S. Appl. No. 09/524,397, filed Mar. 13, 2000.
Copending U.S. Appl. No. 09/524,397, Non-Final Rejection mailed Dec. 18, 200.
Copending U.S. Appl. No. 09/524,397, Response to Office Action Mar. 19, 2001.
Copending U.S. Appl. No. 09/524,397, Final Rejection mailed Jun. 13, 2001.
Copending U.S. Appl. No. 10/076,919, filed Feb. 15, 2002.
Copending U.S. Appl. No. 10/458,117, filed Jun. 10, 2003.
Copending U.S. Appl. No. 10/458,117, Non-Final Rejection mailed Mar. 22, 2005.
Copending U.S. Appl. No. 10/458,117, Response to Office Action Jun. 22, 2005.
Copending U.S. Appl. No. 10/458,117, Final Rejection mailed Sep. 6, 2005.
Copending U.S. Appl. No. 10/458,117, Response to Office Action Nov. 8, 2005.
Copending U.S. Appl. No. 10/458,117, Advisory Actiom Jan. 20, 2006.
Copending U.S. Appl. No. 10/458,117, Request for Continued Examination Feb. 21, 2006.
Copending U.S. Appl. No. 10/458,117, Non-Final Rejection mailed Nov. 15, 2006.
Copending U.S. Appl. No. 10/458,117, Response to Office Action Feb. 13, 2007.
Copending U.S. Appl. No. 10/458,117, Final Rejection mailed May 3, 2007.
Copending U.S. Appl. No. 10/458,117, Request for Continued Examination Aug. 3, 2007.
Copending U.S. Appl. No. 10/458,117, Response to Office Action Aug. 3, 2007.
Copending U.S. Appl. No. 10/458,117, Request for Conitinued Examination Feb. 26, 2008.

(56) References Cited

OTHER PUBLICATIONS

Copending U.S. Appl. No. 10/458,117, Examiner Interview Summary mailed May 16, 2008.
Copending U.S. Appl. No. 11/932,907—RCE Response Sep. 15, 2011.
Copending U.S. Appl. No. 11/258,795 Non-Final Office Action mailed Apr. 26, 2011.
Copending U.S. Appl. No. 11/689,670, RCE Response Sep. 19, 2011.
Copending U.S. Appl. No. 10/614,352, Final Office Action Jul. 12, 2010.
Copending U.S. Appl. No. 11/932,602 Final Response to Office Action Jun. 10, 2011.
Copending U.S. Appl. No. 11/671,556 Response filed Aug. 23, 2010.
Co-pending U.S. Appl. No. 11/438,537, Supplemental Final Rejection mailed Sep. 25, 2009.
Final Office Action dated Jun. 11, 2015 relating to U.S. Appl. No. 13/871,892, 7 pages.
Non-Final Office Action dated Dec. 2, 2014 relating to U.S. Appl. No. 13/871,892, 7 pages.
Final Office Action dated May 14, 2014 relating to U.S. Appl. No. 13/871,892, 10 pages.
Non-Final Office Action dated Sep. 17, 2013 relating to U.S. Appl. No. 13/871,892, 12 pages.
Non-Final Office Action dated Dec. 30, 2015 relating to U.S. Appl. No. 13/871,892, 6 pages.

\* cited by examiner

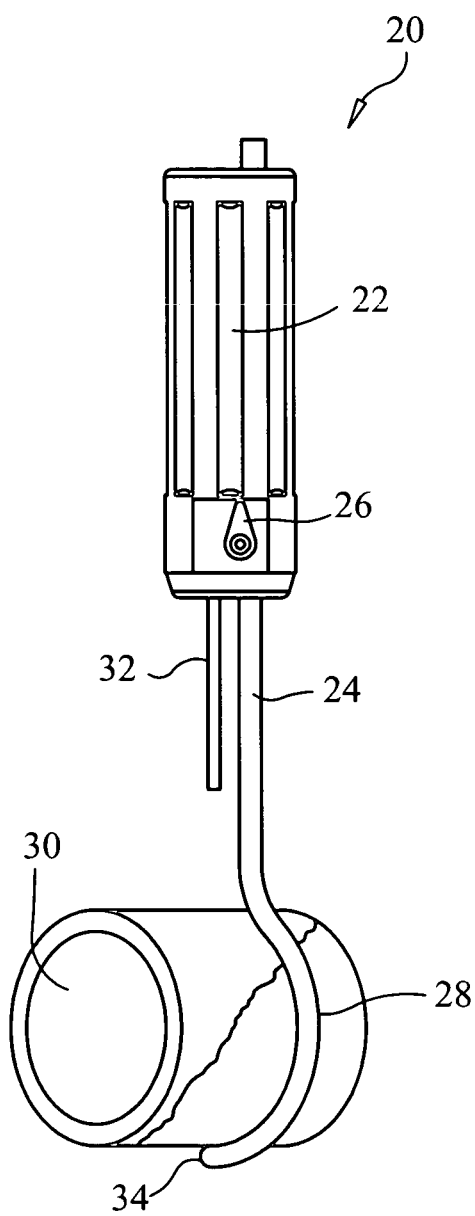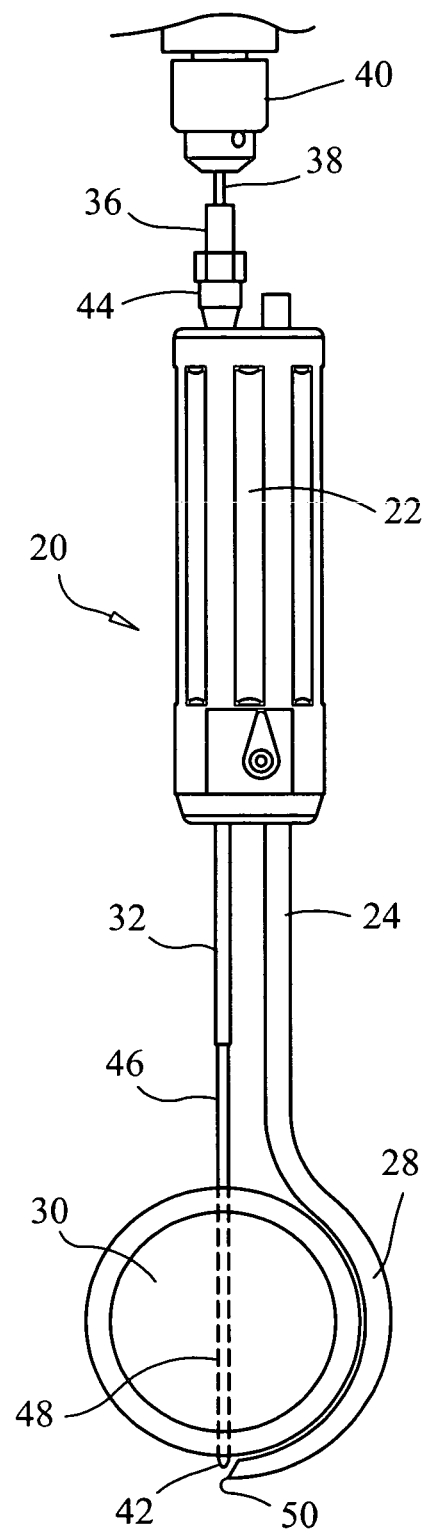
FIG. 1
FIG. 2

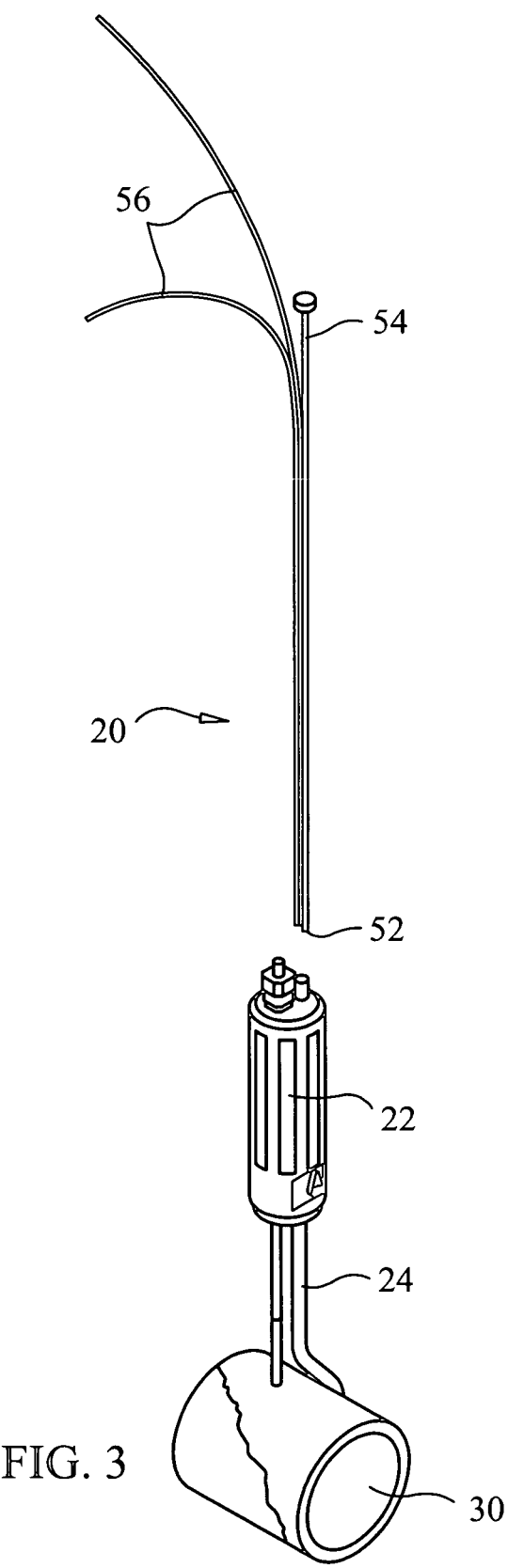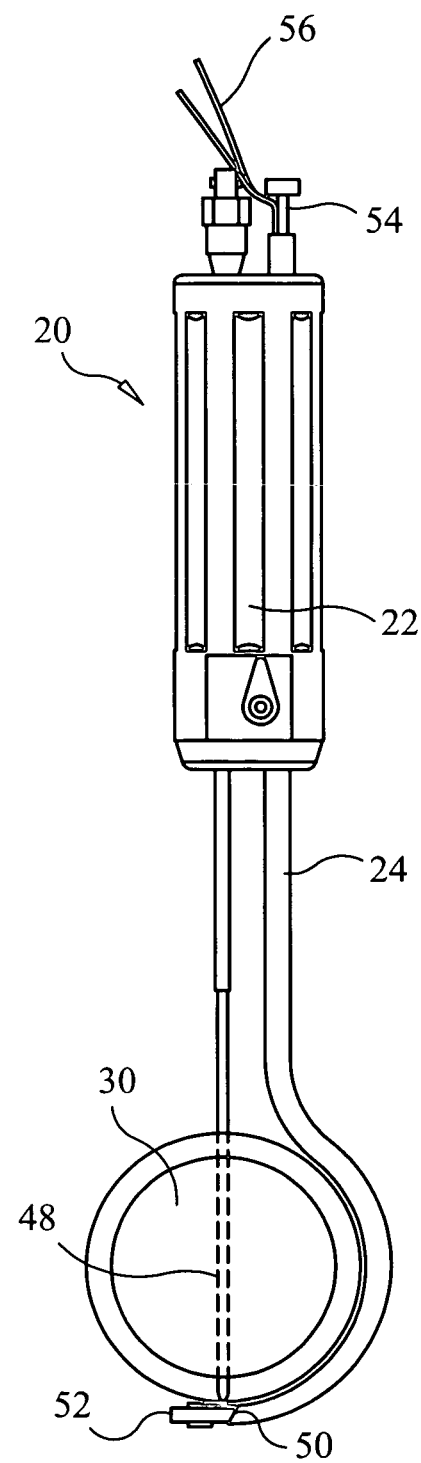
FIG. 3
FIG. 4

APPARATUS FOR GUIDING AND POSITIONING AN IMPLANT

FIELD OF THE INVENTION

The invention relates to apparatus and methods for surgery. More specifically, the invention relates to the guidance and positioning of tissue, an implant, or other surgical devices within the body.

BACKGROUND OF THE INVENTION

In the medical arts, physicians use various methods and devices to attach soft tissue to other soft tissue, soft tissue to hard tissue, and hard tissue to other hard tissue. These same or similar techniques and devices are also used to position or fix an implant within the body. Such implants may include bone plates, fasteners, stents, filters, drug eluting implants, tissue alignment members, organ transplants, tissue scaffolding, tissue grafts, intervertebral disc replacement components, nucleus pulposus replacement component, and other joint replacements components, prostheses, robotic components, nanotechnology devices, sensors, emitters, radiofrequency emitting diodes, computer chips, RFID (radiofrequency identification) tags, adhesives, and sealants.

Applying pressure or compression to tissue and/or an implant helps during the healing process. Incised or torn soft tissue, for example, may be approximated with bandages, sutures, or staples. Proper and more rapid healing of broken or fractured bones likewise may be facilitated by applying constant pressure to the bone. For instance, physicians may insert pins, screws, or bolts in the area of the fracture in order to apply compression and stabilization to the fracture.

However, inserting screws through or around fractures can be complex and time-consuming. For example, the process of inserting a screw typically involves multiple steps conducted from multiple incisions or openings that provide access to the treated bone or tissue, including the steps of drilling holes, measuring the relevant distances to determine the appropriate screw selection, tapping the hole to establish threads, and screwing the screw into the hole.

In addition to the length and complexity of the process, bone screws also may lose their grip and strip out of the bone. Also, currently available lag screws typically provide only one side of cortex fixation and are generally not suited for percutaneus surgery. Moreover, when placing the screws in the bone, the physician may not accurately set the screw into the distal hole or may miss the distal hole completely, thereby resulting in the screw stripping the threads or breaking the bone.

Many devices and instruments have been disclosed to fasten soft and hard tissue for enhanced healing or tissue reconstruction. Examples of such devices include bone plates, bone wraps, external bone supports, and the like.

For example, U.S. Pat. No. 4,257,411 to Cho discloses a surgical drill guide tool adapted to be temporarily mounted about a distal portion of the femur for drilling a bony tunnel through a portion of the femur. The surgical tool allows for very precise location of the drill exit within the intercondylar notch, which is often critical in proper reconstruction of the anterior cruciate ligament of the knee. The surgical tool drill guide is characterized by having a first and second upright, with first and second drill sheaths located at their respective distal ends wherein transverse mounting means are provided to allow the surgeon to position the first and second drill sheaths tightly against opposite surfaces of the femur to provide a continuing and exact alignment for the drilling of the bony tunnel. The drill sheath at the distal end of the second upright is configured to fit inside the intercondylar notch, and allow exact placement of the exit of a bony tunnel which is drilled extra-articularly through the skin, and through the lateral femoral condyle.

U.S. Pat. No. 4,922,897 to Sapega et al. discloses a method and apparatus for the permanent surgical reconstruction of the anterior cruciate ligament in the human knee, which will stabilize the tibia and femur relative to each other and restore a full range of motion to the knee, by precisely locating the ends and angular relationship of a replacement ligament within the knee joint, at bone attachment sites such that the degree of shortening and lengthening experienced by the replacement ligament over the range of joint motion is either as close to zero (isometric) as possible, or closely matches that of the natural uninjured ligament (physometric), whichever the surgeon feels is most desirable.

U.S. Pat. No. 5,573,538 to Laboureau discloses ancillary instruments for the reconstruction of a posterior cruciate knee ligament by drilling one or two tibial canals using a surgical operation performed from the front. The instrument set includes a system for protecting the posterior surface of the upper tibia end and an aiming device for guiding at least one drill. The protection system includes at least one bent tube removably coupled by an extension portion to a locking handle for securing the tube through the intercondylar fossa of the femur on the posterior surface of the upper end of the tibia, so that the distal end of the bent tube serves as the stop to the drill guided by the aiming device and emerging from the tibial bone canal, and the bent tube can form, together with a rectilinear wire feed-through tube disposed in the place of the drill, a continuous canal for guiding a metallic loop used to draw the prosthetic posterior cruciate knee ligament from the anterior surface of the tibia to the femur insertion point.

U.S. Patent Publication No. 2003/0216742 to Wetzler et al. discloses a surgical drill guide generally including a handle connected to an arm with an end that contacts bone. The handle has a plurality of non-parallel channels therein for receiving a sleeve at different angles. Once properly positioned, the sleeve can be used to guide a K-wire into the bone, which can then be used as a guide for drilling a tunnel. The various angles allow the surgeon to achieve a range of tunnel lengths. In some embodiments, the guide has a locking mechanism for locking the sleeve in the channels.

Accordingly, a need exists for a method and device which can provide guided positioning and flexible or rigid fixation of tissue and/or an implant within the body while accessing the procedure site from a small skin portal.

SUMMARY OF THE INVENTION

The present invention provides an instrument and method for guiding and positioning various implants within the body. The instrument may provide for the placement of a biocompatible implant within tissue and/or may provide for dynamic and rigid fixation of tissue. An implant guidance and positioning device includes a body member connected with a hook. The hook may have a lumen extending therethrough. The device also includes a guide channel disposed in the body member. The longitudinal axis of the guide channel may be generally aligned with or slightly offset from a distal end of the hook. The device may further include a pushrod for positioning a fastener and suture in the lumen of the hook. Furthermore, the device may include an elongated claw dimensioned for insertion through the guide channel. The claw may include means for grabbing the suture.

In another embodiment, the positioning device includes a body member, an elongated member connected with the body member, a socket member connected to the distal end of the elongated member, and a guide slot disposed in the body member. The longitudinal axis of the guide slot is generally aligned with or slightly offset with the socket member. The socket member may be dimensioned and configured for holding a fastener. The device may also include a fastening member dimensioned for insertion in the guide slot. The fastening member may include means for attaching the fastening member to the fastener, such as threads, ribs, magnets, adhesives, or expandable material.

In a related aspect of the present invention, the distal portion of the hook or elongated member is curved to be positionable at least partially on the distal or backside of the bone or tissue, while the proximal portion of the hook or elongated member may be generally parallel with the guide channel or slot. The hook or elongated member may be removeably connected with the body member with means for holding and releasing the hook or elongated member.

The positioning device may further include a drill system having a drill bit dimensioned for insertion through the guide channel or slot. The drill system may create a linear or non-linear passage in tissue. The drill system may be a cannulated drill system. The positioning device may also include means for clamping the device to tissue. Such means may include a threaded tube adjustably attached to the body member, a tube and a finger grip attached to the body member, or one or more pins placed between the positioning device and tissue. Furthermore, the device may include a tensioning mechanism for tensioning the suture or fastening member.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 shows an exemplary embodiment of the guidance and positioning device of the present invention;

FIG. 2 illustrates a cannulated drill system inserted in the device;

FIG. 3 shows a pushrod configured for inserting a fastener and suture into a hook of the positioning device;

FIG. 4 illustrates a fastener and suture positioned in the hook;

DETAILED DESCRIPTION OF THE INVENTION

Figure 5:
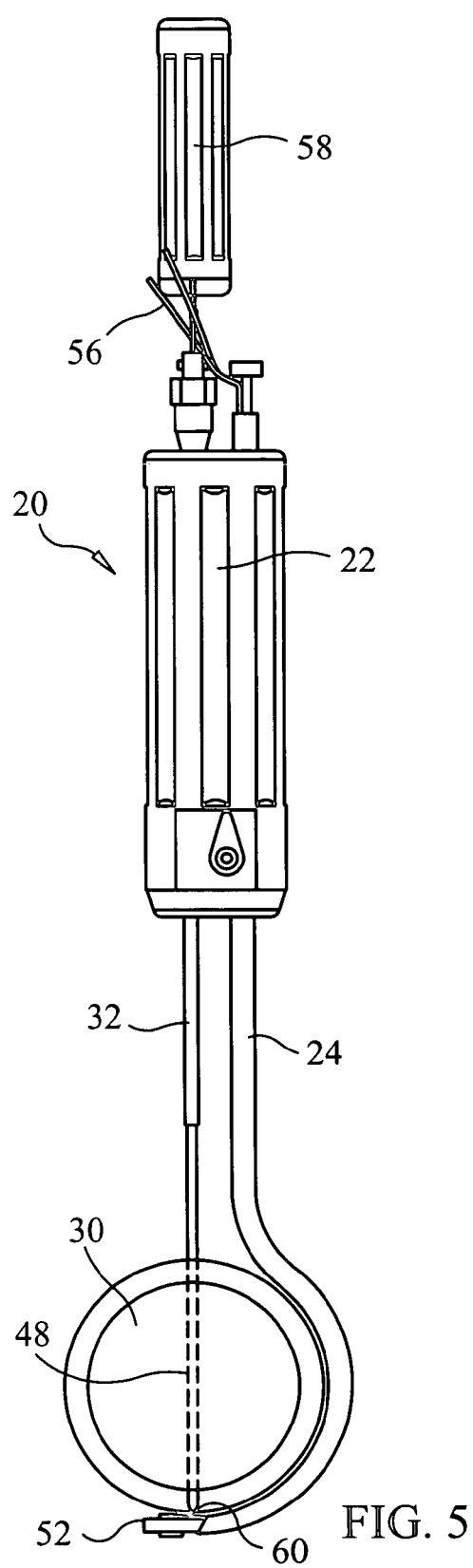
FIG. 5 shows a suture claw positioned in the guide channel of the device.

The present invention provides an instrument and method for guiding and positioning tissue and/or an implant within the body. The instrument may provide for the placement of a biocompatible implant within tissue or may provide for dynamic and rigid fixation of tissue. The device can access and treat a fractured, incised or torn tissue, or the like, from one access area (i.e., from only one opening to the tissue to be fastened) instead of requiring two or more openings. That is, the device is a linear system that can be used with a single, small incision or portal in the skin or other soft tissue to gain access to the tissue, for example a fractured bone.

The guidance and positioning device may be an all-in-one system for creating a passage in tissue, positioning fasteners or other implants, and tensioning an elongated fastening member, like a suture, thread, wire, or pin. In some embodiments, the device may allow for the implantation of multiple sutures and fasteners in tissue with little or no repositioning of the device. For example, the device may have two or more of the elements described below connected to a single grip or handle. Likewise, the incision or opening providing access to the treated bone or tissue may extend at least partially in a direction along the length of the treated area so that the processes described below may be repeatedly performed on other, nearby portions of the bone or tissue in a similar manner.

Tissue Repair

Referring now to the drawing figures in which like reference designators refer to like elements, there is shown in FIG. 1 an exemplary embodiment of the guidance and positioning device 20. The device includes a generally cylindrical handle 22 and a hook 24 with a proximal end connected to the handle 22. In one embodiment, the hook has a tubular construction. An interior passageway may extend from the proximal end to the distal end. The hook 24 may be curved as illustrated in the Figures, may be angular (e.g., may have an open-sided geometric shape), or may have any other desired shape so that its distal end is disposed approximately around the bone or tissue to be treated or fastened.

The proximal portion of the hook 24 may be positioned generally parallel with the longitudinal axis of the handle 22. A plurality of interchangeable hooks 24 may be releasably and interchangeably connected to the handle. In this manner, hooks of different sizes, shapes, or other features may be selected and used as desired by a physician. Thus, the device 20 may have a lever, clip, set-screw, button, spring, match, or latch 26 that allows selective securing and releasing of hooks 24 to or from the handle 22. The lever 26 allows different sized hooks 24 to be placed in the handle 22. For example, the hook may include different sized lumens extending therethrough, may be different lengths, and/or may have different radii of curvature. The curved or angled portion 28 of the hook 24 may be configured for positioning around a fractured bone 30 (as seen in FIG. 1), multiple pieces of similar tissue, multiple pieces of different tissue, or a single tissue element. Examples of such tissue includes, not is not limited to, bone, muscle, cartilage, ligament, tendon, skin, etc. Also, the tissue may be stomach tissue, and the positioning device may be used during bariatric surgery, like gastric stapling. It is further contemplated that measurements such as the depth, angle, length, and/or compression of the hook be determined. The handle may include guides or indicia for measuring and displaying these measurements. Alternatively, the positioning device may include sensors for taking these measurements. For example, the handle of the device may include sensors and/or radiofrequency transmitters for determining and sending measurements to a computer and/or display.

A guide channel 32 extends through the handle 22. Preferably, the guide channel 32 extends generally parallel with the longitudinal axis of the handle 22. The longitudinal axis of the guide channel 32 is generally aligned with or is slightly offset from the distal end 34 of the hook 24. For instance, the shortest distance between the longitudinal axis of the guide channel and the distal end of the hook may be about 2 cm or less. In other embodiments, the shortest distance may be about 1 cm or less, or even about 0.25 cm or less.

Preferably, the guide channel 32 and hook 24 are configured so that the device can be used with a single, small incision in the skin or other soft tissue to gain access to the fractured bone or other tissue requiring fixation. For example, the portions of the guide channel 32 and hook 34 that are near the opening or incision may be spaced apart from each other by about 5 cm or less, and preferably are spaced about 2 cm or less from each other near the incision or opening. In one embodiment, the guide channel and hook are generally parallel and relatively close to each other for a substantial portion of the distance between the handle and the incision or opening.

In use, the device 20 is positioned with the curved portion 28 of the hook 24 placed next to and around the tissue to be fastened. The hook may be positioned subcutaneously, percutaneously, and/or minimally invasively. The tissue may be a fractured bone, a tissue fragment having tendon and bone or ligament and bone, or a tissue with avulsion type fragments. In FIG. 2, a curved portion 28 of the hook 24 is placed around a fractured bone 30 (fracture not shown) or tissue. A drill system 36 is positioned in the guide channel 32. The drill system 36 includes a headpiece 38 configured for attachment to a drill 40. A drill bit 42 is positioned at the distal end of the drill system 36. A drill stop 44 is located distal from the headpiece 38 and prevents the drill bit 42 from penetrating too far beyond the tissue to be drilled. The drill system 36 may be a cannulated drill system. A cannula or sleeve 46 may encircle the drill bit 42 or at least the shaft portion of the drill bit 42. As the drill bit 42 creates a passage 48 through the bone 30, the sleeve 46 is positioned in the passage 48 to link the bone passage 48 and the guide channel 32. The drill system 36 is used to create a passage 48 in the bone 30 from the proximal side of the bone 30 to the distal side of the bone 30, then the drill 40 and drill bit 42 are removed from the sleeve 46 and guide channel 32. The distal opening of the bone passage 48 is generally near the distal aperture 50 of the hook 24.

It is contemplated that the drill system may be used to create a non-linear passage in tissue. The non-linear passage may be formed to go around implants such as an intramedullary rod or prosthesis. The non-linear passage may also allow a physician to avoid critical body parts or tissues such as vessels or organs. Alternatively, no drill system may be employed to create a passage in the tissue. Rather, as described in more detail below, the guide channel may be used to guide and position a self-introducing elongate member like a guide wire, k-wire, claw, grabber, etc. The self-introducing member may be forced through the soft or hard tissue instead of pre-drilling a passage.

Next, as seen in FIG. 3, a fastener 52 is positioned at the distal end of a flexible pushrod 54. The fastener 52 may be connected with the pushrod 54 or may be loosely fitted with the distal end of the pushrod 54. A suture 56 is looped through or connected with the fastener 52 such that one, two, or more sections, legs, strands, or portions of the suture 56 extend from the fastener 52. Examples of fasteners may be found in U.S. Pat. Nos. 5,163,960 and 5,593,425 entitled "Surgical Devices Assembled Using Heat Bondable Materials" which disclose fasteners assembled from a plurality of discrete components, one of which includes a heat bondable material for bonding the components together. The heat bondable material is preferably a polymeric or composite material suitable for surgical applications and implantation in the human body. The heat bondable material may be a biodegradable material. A laser, hot air gun, welding gun, soldering gun, or Bovie tip may be used as a heat source for bonding the fastener. U.S. Pat. No. 6,368,343 entitled "Method of Using Ultrasonic Vibration to Secure Body Tissue" further discloses using ultrasonic vibration energy to bond the heat bondable material of the components of the fastener.

U.S. Pat. No. 5,403,348 entitled "Suture Anchor" discloses an anchor for securing a suture in the body. The anchor includes a tubular wall having a central axis. The tubular wall has a proximal end and a distal end each free of axially inwardly extending slots. The tubular wall also has an inner surface extending for the entire length of the tube and defining in the anchor a central opening extending between the proximal end and the distal end. The anchor has a width less than its length. A suture may extend through the anchor within the central opening. First and second end portions of the suture extend out of opposite ends of the anchor and are sufficiently long to project out of the body when the suture is secured in the body by the anchor. The anchor has an anchoring orientation in the body achieved by manipulation of the distal end of the anchor by pulling on the second end portion of the suture. Furthermore, the anchor has a removal orientation in the body achieved by manipulation of the proximal end of the anchor by pulling on the first end portion of the suture.

U.S. Pat. No. 5,464,426 entitled "Method of Closing Discontinuity in Tissue" discloses a suture anchor having a generally cylindrical configuration with a lumen extending therethrough. In use, a suture is inserted through openings in a plurality of anchors. Pulling on the suture presses the anchors against the body tissue and presses the body tissue together. The anchors may be pushed through the body tissue with a pusher member or by pushing the anchors against each other.

U.S. Pat. No. 5,549,630 entitled "Method and Apparatus for Anchoring a Suture" discloses a tubular anchor having a polygonal cross-sectional configuration with flat outer side surfaces areas connected by a plurality of outer corner portions. A passage through the anchor may be formed by flat inner side surfaces interconnected by inner corner portions. A suture is inserted through the passage. A concentrated force may be applied against a limited area on a trailing end of the anchor to rotate the anchor to move an outer corner portion of the anchor into engagement with body tissue. The suture may engage an inner corner portion of the anchor. The suture may be inserted through a plurality of anchors and the anchors moved through a tubular member into the body tissue under the influence of force transmitted from a trailing anchor to a leading anchor. When the leading anchor is moved into the body tissue, it is rotated under the influence of force applied against a trailing end of the leading anchor. If desired, two anchors may be interconnected. A groove may advantageously be provided along the leading end and side of an anchor to receive the suture.

U.S. Pat. No. 5,713,921 entitled "Suture Anchor" discloses a suture anchor formed from body tissue. The body tissue is shaped to a desired configuration for the anchor and defines a passage through the anchor. A suture is inserted into the passage in the body tissue of the anchor. The anchor is then positioned in a patient's body with a suture extending into the passage in the anchor. The anchor may be formed of osseous body tissue, hard compact bone, dense connective body tissue, or other body tissue. The body tissue may be dried so that it absorbs fluid and expands upon being inserted into a patient's body.

U.S. Pat. No. 5,718,717 also entitled "Suture Anchor" discloses an anchor formed of a material which absorbs body liquid when exposed to body liquid. The anchor may be at least partially formed of a material having a strong affinity for body liquids. This enables the anchor to absorb body liquid and expand upon being inserted into a patient's body. At least one embodiment of the suture anchor has portions formed of a relatively hard material which does not absorb body liquids and is pressed against body tissue by the material which absorbs body liquid to mechanically interlock the suture anchor and the body tissue. The anchor may be at least partially formed of a cellular material. The cells expand to absorb body liquid. At least one embodiment of the anchor has a pointed leading end portion to form an opening in an imperforate surface on body tissue. The configuration of the anchor may be changed by tensioning the suture while the anchor is disposed in body tissue.

U.S. Pat. No. 5,782,862 entitled "Suture Anchor Inserter Assembly and Method" discloses a suture anchor inserter assembly including a manually engageable handle and a shaft which extends axially outward from the handle. The shaft includes an inner member which is fixedly connected with the handle and an outer member which is retractable into the handle. An anchor is received in a chamber formed at the outer end of the shaft.

U.S. Pat. No. 5,814,072 entitled "Method and Apparatus for Use in Anchoring a Suture" discloses a suture anchor inserter including a manually engageable handle and a shaft which extends from the handle through a passage in the anchor. During insertion of the anchor into body tissue, an end portion of the shaft pierces the body tissue in advance of the anchor. At the same time, a pusher surface on the shaft applies force against a trailing end portion of the anchor to push the anchor into the body tissue. When the orientation of the anchor is to be changed, rotational force is applied to the anchor by tensioning the suture and pressing the end portion of the shaft against an inner surface of the passage in the anchor.

U.S. Pat. No. 5,814,073 entitled "Method and Apparatus for Positioning a Suture Anchor" discloses an inserter assembly operable between a closed condition blocking movement of a suture anchor through the inserter assembly and an open condition in which the inserter assembly is ineffective to block movement of the anchor.

U.S. Pat. No. 5,845,645 entitled "Method of Anchoring a Suture" discloses a process of fastening a suture to an anchor. The suture is inserted through passages which are spaced apart along and extend transversely to a longitudinal central axis of an anchor. When the anchor is moved into body tissue, a first portion of the suture extends from the first passage in the anchor through an opening in the body tissue to a location disposed to one side of the body tissue. A second portion of the suture extends from the second passage in the anchor through the opening in the body tissue. The suture is tensioned to apply force to the anchor. The force applied to the anchor by the suture initiates tipping of the anchor and movement of an end surface on the anchor across a leading end surface on an inserter member.

U.S. Pat. No. 5,921,986 entitled "Bone Suture" discloses an anchor connected with a suture moved through a passage between opposite sides of a bone. The anchor is then pivoted to change its orientation. A second anchor is connected with the suture. While tension is maintained in the suture, the suture is secured against movement relative to the anchors. This may be done by tying the suture or by using a suture retainer to hold the suture. A suture retainer may be used in place of the second anchor.

U.S. Pat. No. 5,948,002 entitled "Apparatus and Method for Use in Positioning a Suture Anchor" discloses an apparatus which includes a tubular outer member and an inner or pusher member. During assembly of the apparatus, a suture is positioned in a slot in the outer member. During use of the apparatus, the slot facilitates visualization of the position of the suture anchor relative to body tissue. In addition, the slot facilitates separation of the apparatus from the suture after the suture anchor has been positioned in the body tissue. A suture anchor retainer may be provided at one end of the tubular outer member to grip the suture anchor and hold the suture anchor in place during assembly. The tubular outer member may be utilized to guide a drill during formation of an opening in body tissue and may be subsequently utilized to guide movement of a suture anchor into the opening in the body tissue.

U.S. Pat. Nos. 6,010,525; 6,159,234; and 6,475,230 entitled "Method and Apparatus for Securing a Suture" disclose improved method to secure a suture relative to body tissue. A suture retainer is moved along first and second sections of a suture toward the body tissue. When a predetermined minimum force is being transmitted between the suture retainer and the body tissue, the first and second sections of the suture are gripped with the suture retainer by plastically deforming material of the suture retainer. The material of the suture retainer cold flows under the influence of force applied against the surface areas on the suture retainer. One or more bends are formed in each of the sections of the suture to increase the holding action between the suture retainer and the sections of the suture. The bends may be formed by wrapping a turn of the suture around a portion of the suture retainer. During movement of the suture retainer toward the body tissue, the bends are moved along the first and second sections of the suture.

U.S. Pat. No. 6,045,551 entitled "Bone Suture" discloses an anchor connected with a suture moved through a passage between opposite sides of a bone. The anchor is then pivoted to change its orientation. A second anchor is connected with the suture. While tension is maintained in the suture, the suture is secured against movement relative to the anchors. This may be done by tying the suture or by using a suture retainer to hold the suture. A suture retainer may be used in place of the second anchor. The passage may extend across a fracture in the bone. The passage may have either a nonlinear or linear configuration. A tubular member may be positioned in the passage with the tubular member extending into portions of the passage on opposite sides of the fracture. Opposite end portions of the tubular member may be disposed in a compact outer layer of the bone. If desired, a member other than a suture may be used as a force transmitting member between the two anchors. The tubular member may be formed of bone.

U.S. Pat. No. 6,447,516 entitled "Method of Securing Tissue" discloses a retainer member formed of bone which secures tissue against movement relative to a portion of a bone in a patient's body. The retainer member is utilized to form an opening in a compact outer layer of a portion of the bone in the patient's body. The retainer member formed of bone is advantageously enclosed in a tubular member or sleeve to prevent breaking of the retainer member during the forming of the opening in the bone. The extent of movement of the retainer member into the bone in the patient's body is determined as the retainer member is moved into the bone. A suture may be connected with the retainer member and used to connect tissue with the bone.

U.S. Pat. No. 6,592,609 entitled "Method and Apparatus for Securing Tissue" discloses an anchor having a pointed end portion may be utilized to form an opening in a bone in a patient's body. The anchor is moved into the opening formed in the bone in the patient's body with a suture connected to the anchor. The suture may then be utilized to retain body tissue in a desired position relative to the bone. The body tissue may be either hard or soft body tissue. If desired the anchor may be utilized in conjunction with layers of soft body tissue. When a suture is used it may be secured by connecting a retainer with the suture. Alternatively, sections of the suture may be interconnected. It is believed that it may be preferred to secure the suture in place after at least a predetermined tension has been established in the suture and/or a predetermined force has been transmitted to the body tissue. The suture may be secured in place by exposing a retainer to ultrasonic vibratory energy or by applying the ultrasonic vibratory energy directly to sections of the suture.

U.S. Pat. No. 6,635,073 entitled "Method of Securing Body Tissue" discloses a process to secure a first body tissue with a second body tissue. A first anchor is moved along a first path through the first body tissue into the second body tissue. A second anchor is moved along a second path through the first body tissue into the second body tissue. A suture extending between the anchors may be tightened by moving the second anchor along a path which extends transverse to the path of the first anchor. The suture which extends between the anchors may have free ends which are connected with a suture retainer. The free ends of the suture may be interconnected either before or after the anchors are moved along the first and second paths. Alternatively, the suture may be a continuous loop which extends between the two anchors. A guide assembly may be provided to guide movement of the anchors along the two paths. The paths along which the anchors move may intersect so that the anchors may be interconnected at the intersection between the two paths.

U.S. Pat. No. 6,719,765 entitled "Magnetic Suturing System and Method" discloses an instrument and method for passing a medical implement through tissue with magnetic forces. The implement can be an implant, either permanent or temporary, and is provided with a magnetic component. A magnetic field is established and the magnetic component and/or magnetic field is manipulated to drive the implant through tissue. Alternatively, the instrument itself is the implement and includes at least one magnetic element so that a magnetic field established by an external magnetic generator drives the instrument through tissue. In another embodiment, the instrument includes two magnetic elements that are moveable with respect to one another and interaction between the magnetic elements drives the instrument through the tissue. Examples of applications of the present invention include a suture passer and a tissue anchor.

Other fastener types and fastening methods are disclosed in U.S. patent application Ser. No. 10/102,413 entitled "Methods of Securing Body Tissue" which discloses an improved method of securing body tissue performed with a robotic mechanism. The robotic mechanism may be utilized to tension a suture with a predetermined force and urge a suture retainer toward body tissue with a predetermined force. Ultrasonic vibratory energy may be transmitted to the suture retainer to effect a gripping of the suture by the suture retainer. The body tissue may be secured with a staple. Legs of the staple may be bonded together to secure the staple. The legs of the staple may be bonded together by transmitting ultrasonic vibratory energy to the legs of the staple. A tissue positioning assembly may be used to hold the body tissue in a desired position. Images of the body tissue being secured may be obtained using various known devices including one or more endoscopes, a fluoroscope, a magnetic resonance imaging device, and/or other known imaging devices.

U.S. patent application Ser. No. 10/228,855 entitled "Apparatus and Method for Securing a Suture" discloses a suture retainer having an upper or cover section and a lower or base section which cooperate to define passages through which portions of a suture extend. Projections on the cover section of the retainer extend into recesses on the base section of the retainer. A center projection on the base section extends between the two projections on the cover section. The projections cooperate with surfaces on body sections of the cover and base section of the retainer to position and grip portions of the suture. The retainer may be moved along the portions of the suture while the retainer is gripped by an applicator assembly. The applicator assembly is operable to apply energy to the retainer to bond end portions of the projections on the cover section to bottoms of recesses in the base section of the retainer.

U.S. patent application Ser. Nos. 10/779,978; 10/780,444; and 10/797,685 entitled "Method and Device for Securing Body Tissue" disclose sutures and suture retainers positioned relative to body tissue. Energy, such as ultrasonic vibratory energy, is utilized to heat the suture retainer and effect a bonding of portions of the suture retainer to each other and/or to the suture. Portions of the body tissue may be pressed into linear apposition with each other and held in place by cooperation between the suture and the suture retainer. The suture retainer may include one or more portions between which the suture extends. The suture retainer may include sections which have surface areas which are bonded together. If desired, the suture may be wrapped around one of the sections of the suture retainer. The suture retainer may be formed with a recess in which the suture is received. If desired, the suture retainer may be omitted and the sections of the suture bonded to each other.

The characteristics and features of the fasteners and fastening methods just described may be combined and integrated with the devices and methods of the present invention. The above cited patents and patent applications are incorporated herein by reference.

Furthermore, the fasteners may be, but are not limited to, degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, Morse taper single piece, multi-component, solid, hollow, polygon-shaped, pointed, locking and unlocking, self-introducing, knotless, and combinations thereof. Also, the fasteners may include metallic material, polymeric material, ceramic material, composite material, body tissue, synthetic tissue, hydrophilic material, expandable material, compressible material, heat bondable material, biocompatible adhesive, and combinations thereof. Examples of body tissue include bone, collagen, cartilage, ligaments, or tissue graft material like xenograft, allograft, autograft, and synthetic graft material. The fasteners may also be made from a porous matrix or mesh of biocompatible and bioresorbable fibers acting as a scaffold to regenerate tissue.

The fasteners may also be made of or have a coating made of an expandable material. The material could be compressed then allowed to expand. Alternatively, the material could be hydrophilic and expand when it comes in contact with liquid. Examples of such expandable materials are PEEK, ePTFE, and desiccated body tissue. It is contemplated that the fasteners and implants of the present invention may include any combination of materials and agents disclosed herein. For example, a fastener may include combinations of hydrophilic material, synthetic body tissue, collagen, synthetic collagen, heat bonded material, biocompatible adhesive, and cells, such as stem cells.

Moreover, the fasteners described herein and incorporated by reference may include therapeutic substances to promote healing. These substances could include antibiotics, hydroxypatite, anti-inflammatory agents, steroids, antibiotics, analgesic agents, chemotherapeutic agents, bone morphogenetic protein (BMP), tissue inductive factors, demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the fasteners to produce a composite fastener or implant. Alternatively, the therapeutic substances may be impregnated or coated on the fastener. Time-released therapeutic substances and drugs may also be incorporated into or coated on the surface of the fastener. The therapeutic substances may also be placed in a bioabsorbable, degradable, or biodegradable polymer layer or layers.

In addition to including the materials and agents previously described, a fastener may take the configuration of an integrated fastener and arm member. The flexible arm may be incorporated into the fastener and extend therefrom. The arm may be connected with an end portion of the fastener or with any portion between the end portions, like the midpoint. The fastener and flexible arm may include the same or different materials and/or therapeutic agents. In use with the positioning device of the present invention, the fastener may be positioned at the distal end of the hook with the flexible arm extending from the fastener either within the lumen of the hook or exterior to the hook. Once the fastener is properly placed within the body, the flexible arm may be positioned through or around tissue and/or an implant and tensioned to compress and stabilize the tissue and/or implant. Another fastener may be connected with the flexible arm to maintain tension and position of the arm.

The sutures of the present invention may be made of metallic material, non-metallic material, composite material, ceramic material, polymeric material, copolymeric material, or combinations thereof. The sutures may be degradable, biodegradable, bioabsorbable, or nonbiodegradable. Examples of suture materials are polyethylene, polyester, cat gut, silk, nylon, polypropylene, linen, cotton, PLA, PGA, caprolactam, and copolymers of glycolic and lactic acid. Preferably, the sutures are flexible or bendable. They may be threadlike, monofilament, multifilament, braided, or interlaced. The sutures may have a coating of therapeutic substances or drugs. For example, the sutures may include antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

With the fastener 52 and suture 56 on the distal end of the flexible pushrod 54, the pushrod 54 is moved distally through the lumen of the hook 24 until the fastener 52 is positioned generally next to the distal opening of the bone passage 48, as seen in FIG. 4. The pushrod 54 may be advanced to push the fastener 52 beyond the distal aperture 50 of the hook 24 or may be advanced to position the fastener 52 partially in and partially out of the hook 24. In the latter configuration, the fastener 52 may be easily withdrawn, if necessary, from the hook 24 by moving the pushrod 54 proximally.

Alternatively, the fastener 52 and suture assembly may be assembled in the lumen prior to inserting the device in a patient. For example, a suture may be threaded into the lumen from the distal end of the hook 24, or may be inserted through the proximal end as described above before inserting the hook into the patient's body. This allows visual confirmation of that the fastener is in a desired position before introducing it into the patient's body. The hollow interior of the hook 24 may be sized to allow sutures to be placed therethrough, but sufficiently small to preclude the fastener 52 from entering it. The distal end may have a bracket or assembly that holds the fastener 52 in a desired position. The bracket or assembly may grip the fastener in place, such as by an interference fit or with friction. In one embodiment, application of tensioning forces to the suture helps hold the fastener 52 in a desired position relative to the distal end of the hook 24.

As illustrated in FIG. 5, a suture claw or grabber 58 is positioned in the guide channel 32 and through the bone passage 48. A hook, claw, or clip 60 is attached to the distal end of the suture claw 58. When the suture claw 58 is inserted distally into the guide channel 32, the hook or clip 60 exits or at least partially exits the distal opening of the bone passage 48. Since the fastener 52 is positioned near the distal opening of the bone passage 48, the hook or clip 60 of the suture claw 58 can grab or capture the suture 56 extending from the fastener 52. The suture 56 may be grabbed by rotating the suture claw 58 and allowing the suture 56 to wrap around the hook 60 at the distal end of the suture claw 58. Alternatively, the suture 56 may be grabbed with a clip 60, like an alligator clip, which may be activated from the proximal end of the suture claw 58. In another embodiment, a spiral member, like a corkscrew, may be disposed on the distal end of the suture claw. The suture claw may be twisted to thereby allow the spiral member to grab the suture. It should be understood that the suture claw should grab all the suture legs or portions attached to the fastener. For example, in FIG. 5, there are two suture legs extending from the fastener. Both legs should be captured by the suture claw either simultaneously or sequentially.

It is also contemplated that the fastener or suture may be pulled or placed in position using magnetic or electromagnetic force. For example, once a passage is drill through tissue or an implant, a magnetic may be used to pull a suture through the passage. Alternatively, when using a fastener with a flexible arm, the arm may be pulled through the passage. In these embodiments, the suture or flexible arm may include a material which is attracted to a magnet.

As previously described, a passage may not need to be pre-drilled into the tissue or bone. In this instance, the suture claw may include a distal tip configured for penetrating into and through the tissue. Using a self-introducing suture claw eliminates the need to bore a passage through the tissue before pulling the suture through the tissue.

Figure 6:
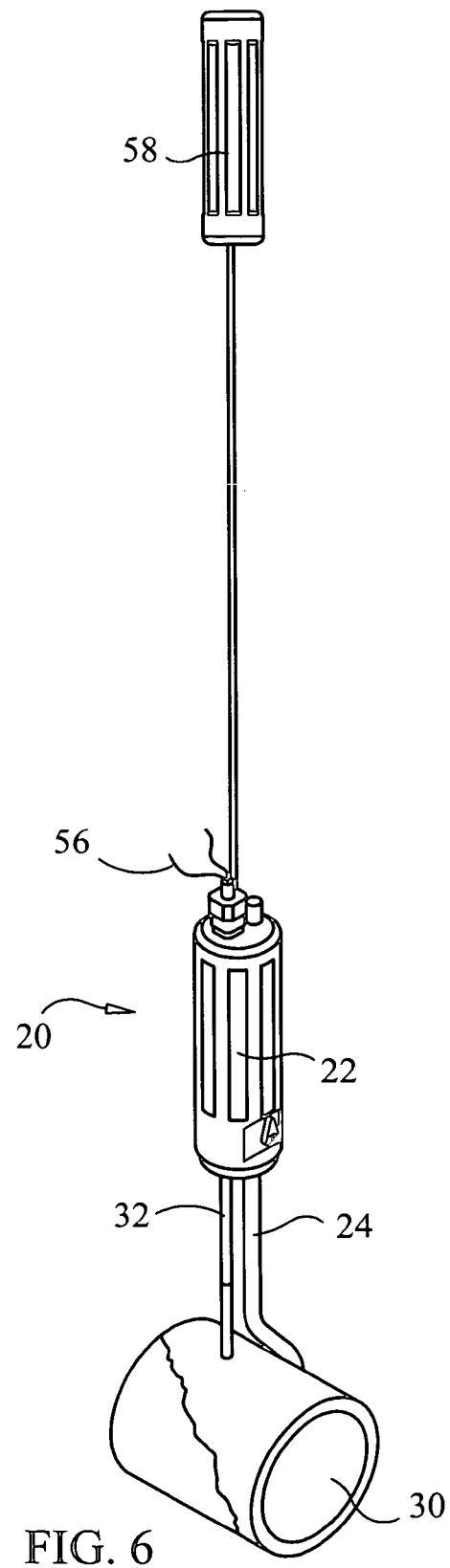
FIG. 6 illustrates the suture claw withdrawn from the guide channel with the suture disposed in the guide channel.
Figure 7:
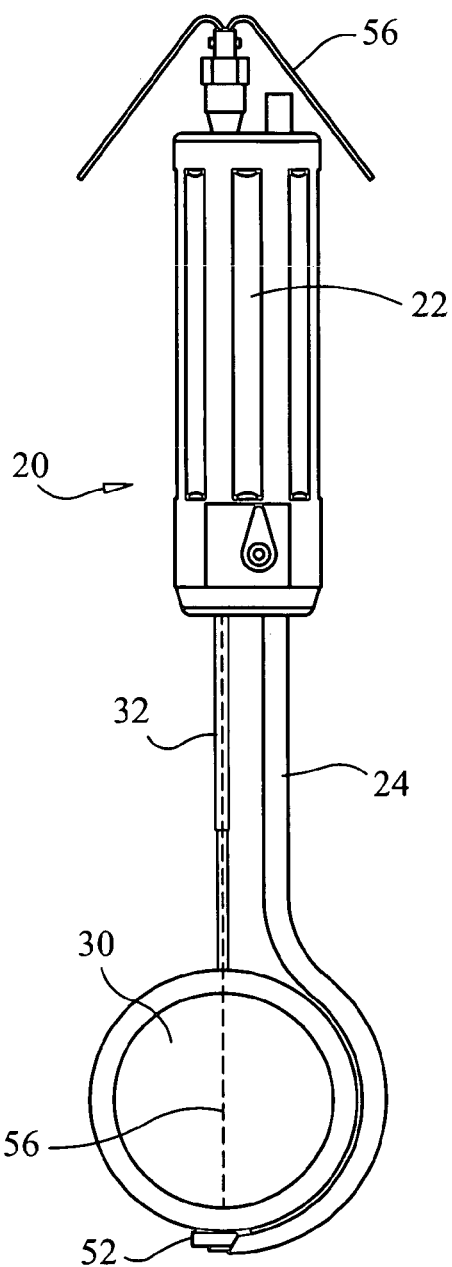
FIG. 7 shows the suture connected with the fastener on the distal side of the bone and the suture extending from the drill system.

In FIG. 6, the suture claw 58 is shown retracted from the guide channel 32. As the suture claw 58 is retracted, it pulls the suture and/or suture portions 56 from the lumen of the hook 24 and into the guide channel 32. As seen in FIG. 7, the proximal ends of the suture portions 56 may extend beyond the proximal end of the guide channel 32 when the suture claw is fully retracted.

Figure 8:
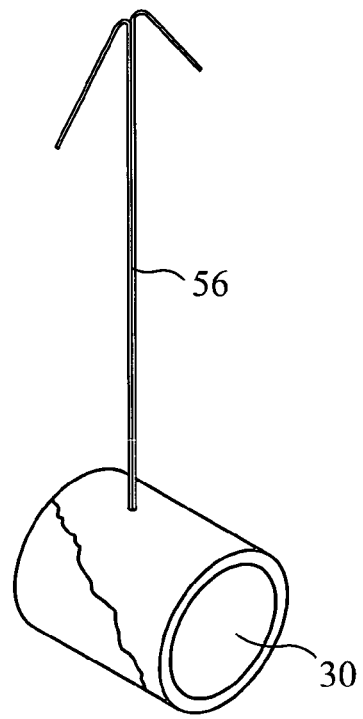
FIG. 8 illustrates a fractured bone with the suture extending therethrough.
Figure 9:
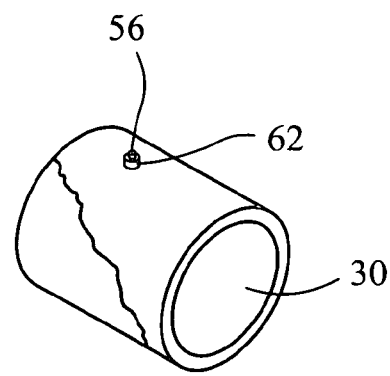
FIG. 9 shows a fastener positioned on the proximal side of the bone and secured to the suture.

As illustrated in FIG. 8, the hook, handle, and drill sleeve of the drill system are removed from the bone 30. The fastener 52 (not shown) is located on the distal side of the bone 30. The suture 56 extends from the fastener 52 through the bone passage and out the proximal opening of the bone or tissue passage. In FIG. 9, another fastener 62 is placed around or otherwise connected with the suture and/or suture portions 56. The suture 56 is tensioned, and the fastener 62 is secured to the suture 56 to thereby approximate the fracture and stabilize the bone 30. The tension of the suture pulls on the fasteners 52 and 62 generally towards each other, thereby applying pressure to the fractured bone or tissue.

Figure 10:
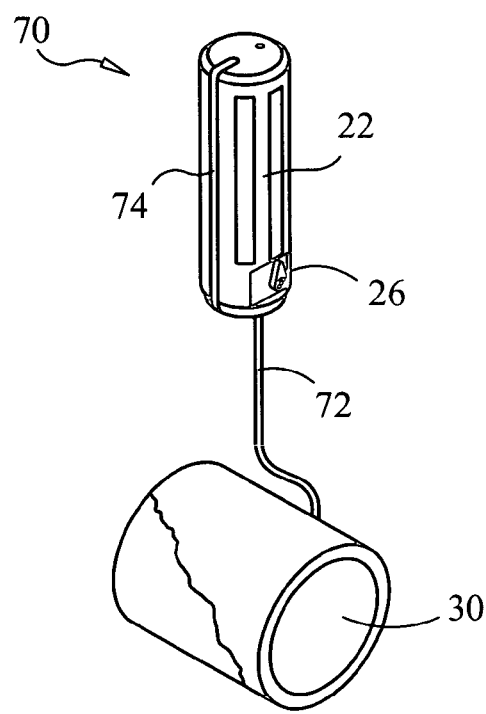
FIG. 10 illustrates another embodiment of the implant guidance and positioning device.

Another exemplary embodiment of the guidance and positioning device 70 is illustrated in FIG. 10. The device 70 is shown positioned around a fractured bone 30. It should be understood that the device may be used to fasten any tissue type or combination of tissues as previously described. The device 70 includes a generally cylindrical handle 22 and a hookshaped elongated member 72 attached to the handle 22. In this embodiment, the hook-shaped elongated member 72 does not necessarily include a lumen extending therethrough. The proximal portion of the hook-shaped member 72 may be positioned generally parallel with the longitudinal axis of the handle 22. The device 70 may include a lever, clip, set-screw, button, spring, or latch 26 for securing and releasing the hook-shaped elongated member 72. The lever 26 allows different sized hooks to be placed in the handle 22. For example, the hooks may be of different lengths, have different radii of curvature, or have different types or sizes of bone engagement portions 28.

A guide slot 74 extends through the handle 22 generally parallel with the longitudinal axis of the handle 22. The longitudinal axis of the guide slot 74 is generally aligned with the distal end of the hook-shaped member 72. The guide slot 74 and hook-shaped member 72 are generally parallel and relatively close to each other at and just distal to the handle 22. In this configuration, a single, small, percutaneous incision may be made in skin or other soft tissue to gain access to the fractured bone or other tissue requiring fixation.

Figure 11:
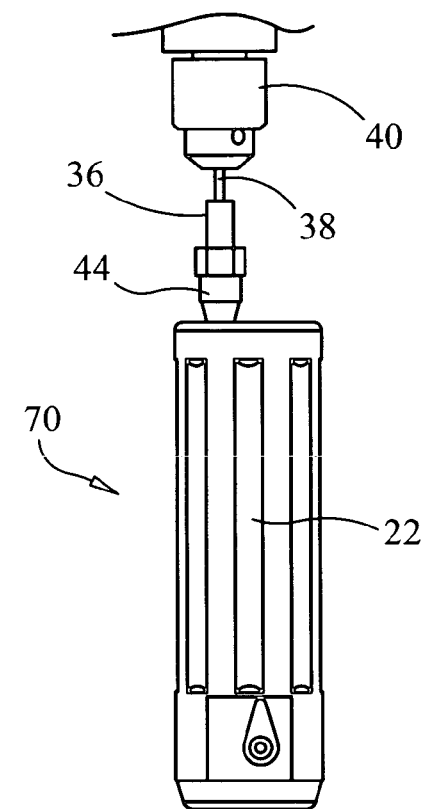
FIG. 11 shows a cannulated drill system disposed in a guide slot of the device.

In use, the device 70 is positioned with the hook-shaped portion 76 of the hook-shaped elongated member 72 placed next to and around the tissue to be fastened. In FIG. 11, the hook-shape portion 76 is placed around a fractured bone 30 (fracture not shown). A drill system 36 is positioned in the guide slot. The drill system 36 includes a headpiece 38 configured for attachment to a drill 40. A drill bit 42 is positioned at the distal end of the drill system 36. A drill stop 44 is located distal from the headpiece 38 and prevents the drill bit 42 from penetrating too far beyond the tissue to be drilled. The drill system 36 may be a cannulated drill system. The drill system 36 is used to create a passage 48 in the bone 30 from the proximal side of the bone 30 to the distal side of the bone 30. The distal opening of the bone passage 48 is generally near a socket 78 at the distal end of the hook-shaped portion 76 of the elongated member 72.

As previously noted, a drill system may not be needed to form a passage in the tissue. An elongated member with a distal tip configured for penetrating through tissue may be placed in the guide slot and used for passage through tissue. The elongate member may be a guide wire, k-wire, needle, or like device.

Figure 12:
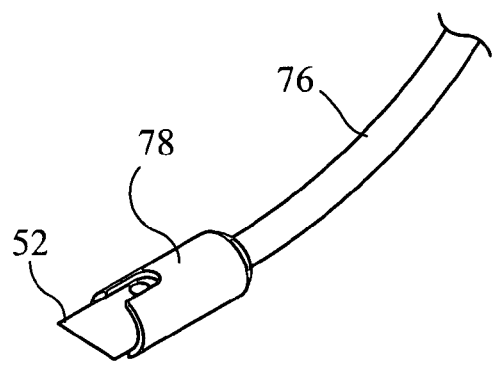
FIG. 12 illustrates a fastener disposed in a socket on the distal end of a hookshaped member of the device.

FIG. 12 illustrates the socket 78 at the distal end of the hook-shaped portion 76 of the elongated member. The socket 78 is dimensioned and configured for holding and/or carrying a fastener 52. The socket 78 may be a hollow cylinder or any other configuration capable of accepting a fastener 52. As seen in FIG. 11, the socket 78 is positioned at the distal end of the hook-shaped member 72 such that the fastener 52 is generally aligned with the distal opening of bone passage 48. The fastener may include characteristics, materials, therapeutic substances, coatings, or any other features as previously described herein. It is contemplated that the socket may hold the fastener magnetically, frictionally, with an interlocking mechanism such as a snap, with adhesive, etc.

Figure 13:
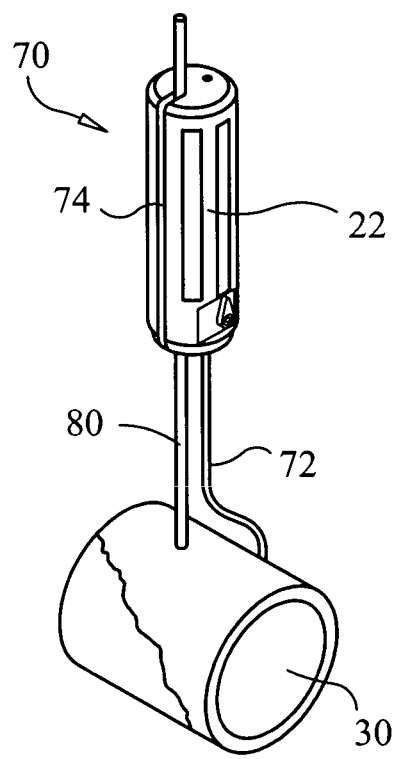
FIG. 13 shows a fastening member positioned in the guide slot of the device.
Figure 14:
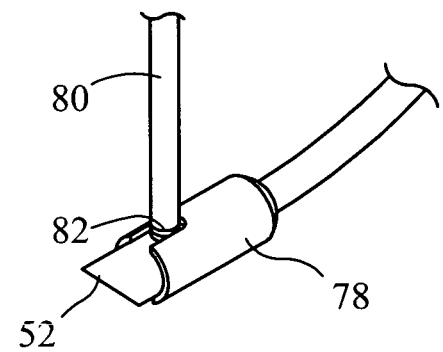
FIG. 14 illustrates a threaded distal portion of the fastening member disposed in a threaded hole of the fastener.

Next, as shown is FIG. 13, the drill system is removed from the guide slot 74. A fastening member 80 is placed in the guide slot 74 and through the passage in the bone 30. The fastening member 80 is moved distally through the passage and inserted into the fastener disposed in the socket at the distal end of the hook-shaped member 72. The fastening member may be made of metal, polymer, ceramic, composite, body tissue, or combinations thereof. The fastening member may also include features, therapeutic agents, and coatings similar to the fastener and suture previously described. FIG. 14 illustrates one exemplary embodiment of the connection between the fastening member 80 and the fastener 52. The distal end of the fastening member includes a threaded portion 82, and the fastener 52 includes a threaded hole. The fastening member 80 is screwed into the fastener 52. Other examples of connecting the fastening member and fastener include ball and socket, hook and loop, mechanical expansion, material expansion, dovetail, orientation change, heat bondable material, biocompatible adhesive, and other similar connection means.

In the embodiment wherein a drill system is not used create a passage in the tissue, the fastening member 80 may include a sharp or pointed distal tip to allow the member to be moved through the tissue, free of a passage. Using a self-introducing fastening member may eliminate the need to pre-drill the passage in the tissue.

Figure 15:
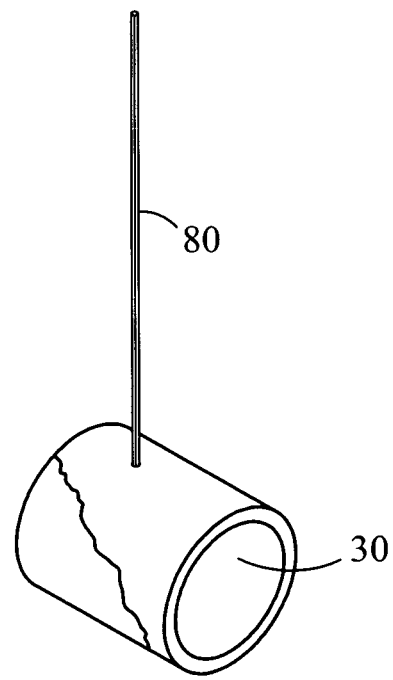
FIG. 15 shows a fractured bone with the fastening member extending therethrough.
Figure 16:
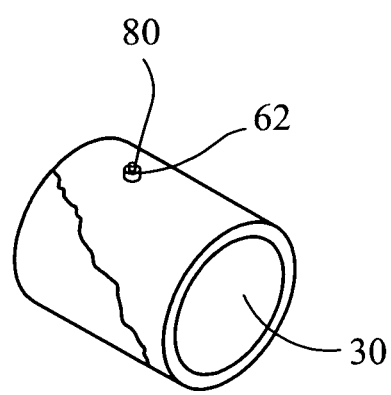
FIG. 16 illustrates a fastener positioned on the proximal side of the bone and secured to the fastening member.

As illustrated in FIG. 15, the guidance and positioning device is removed from the bone 30. The fastener 52 (not shown) is located on the distal side of the bone 30. The fastening member 80 extends through the bone passage and out the proximal opening of the bone passage. In FIG. 16, another fastener 62 is placed around the fastening member 80. The fastening member 80 is tensioned, and the fastener 62 is secured to the fastener member 80 to thereby approximate the fracture and stabilize the bone 30. Once again, the tension of the fastening member pulls the fasteners toward each other, which in turn causes pressure to be applied to the treated bone or tissue.

It is further contemplated that the guidance and positioning device 20, 70 may be used without a distal fastener. In this embodiment, the device 20,70 is used to position a suture on the backside or distal portion of the tissue. The suture claw, grabber, or elongate member may be placed in the guide channel or guide slot and moved distally toward the suture located at the distal end of the hook. Using the suture claw, one or two sections of the suture may be pulled through the tissue to the proximal side of the tissue.

The suture or sutures may be pulled through a pre-drilled passage created by a drill system or may be pulled through a passage created by a self-introducing suture claw. Once a portion of the suture is positioned on the proximal side of the tissue, it may be tensioned and secured with a fastener. Alternatively, the proximally extending suture section may be fastened with another section of the suture extending from the distal end of the hook and around the tissue. In this embodiment a suture loop is formed with tissue caught or positioned in the middle of the loop. The two sections of the suture may be secured with a knot or a fastener.

Figure 17:
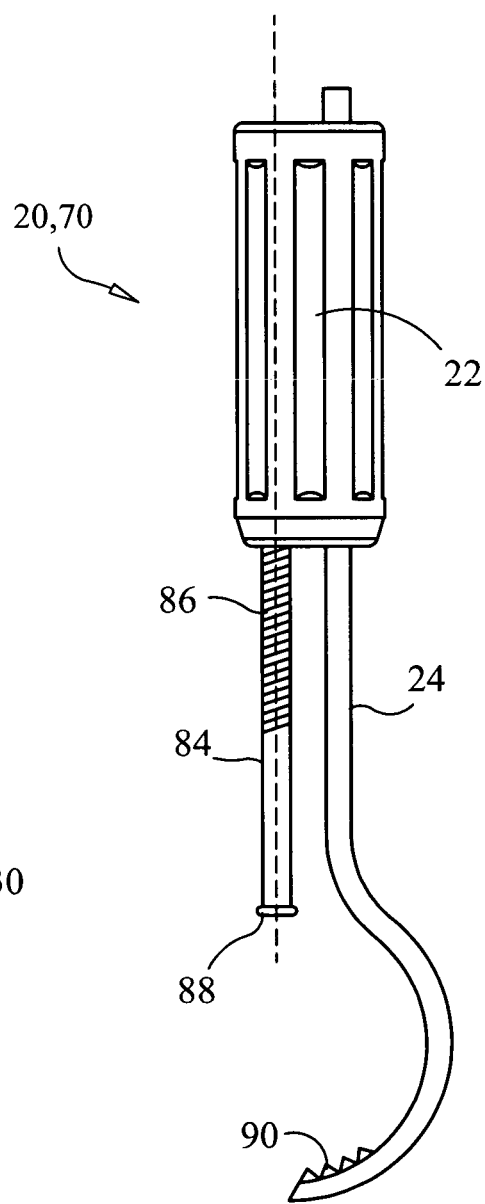
FIG. 17 shows one embodiment of a clamping mechanism of the device.
Figure 18:
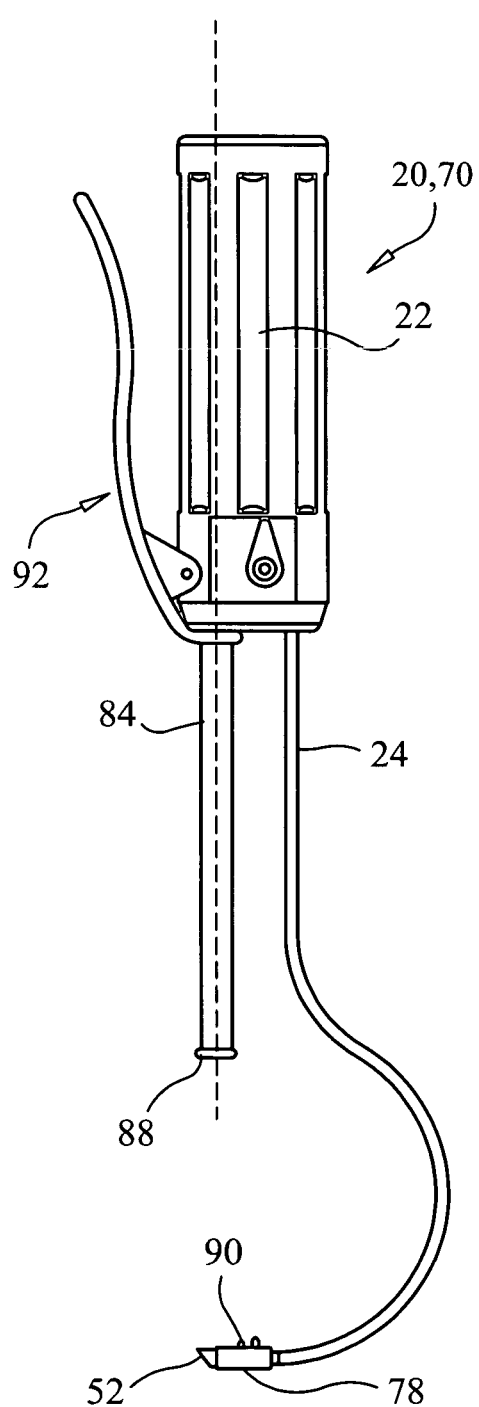
FIG. 18 illustrates another embodiment of the clamping mechanism of the device.

FIGS. 17 and 18 illustrate exemplary embodiments of clamping mechanisms for the guidance and positioning device. FIG. 17 shows a tubular clamp member 84 connected with the handle 22 of the device 20,70. The clamp member 84 includes a lumen extending therethrough for allowing passage of the drill system, suture claw, and suture as previously described. The proximal portion of the clamp member 84 includes threads 86, a ratchet, or the like for advancing the clamp member 84 into and out of the handle 22. The distal end of the clamp member 84 may include a tissue pad 88 for contacting tissue.

The tissue pad 88 may be integrally formed on the distal end of the clamp member. For example, during fabrication of the clamp member, its cross-section may initially be relatively the same size along its length, including at the distal end. Subsequently, the distal end may be deformed or flattened to have a larger cross section.

Alternatively, the tissue pad 88 also may be connected to the clamp member in a manner that allows it to rotate and/or swivel. As the clamp member 84 is moved toward the bone or tissue, some areas of the tissue pad 88 may begin to make contact even though the clamp member 84 may require additional rotation or advancement in order to obtain a desired amount of contact. If the tissue pad 88 is able to rotate or swivel, it can adjust to the contours of the bone or tissue while also reducing potential abrasion.

The contact surface of the tissue pad 88 may be substantially flat, as shown in FIG. 17, but it also may be curved or have a different shape that may correspond generally to the curvature or shape of the bone or tissue that it may contact. The contact surface also may be deformable so that it can more easily conform to an uneven surface of bone or tissue. The deformable surface of the tissue pad may be formed from a layer of elastomeric material (e.g., rubber or urethane), foam material, or any other elastomeric material suitable for use in a surgical procedure.

In use, the device 20 is positioned about a bone, or other tissue. The clamp member 84 is moved or rotated distally so that the tissue pad 88 contacts the proximal side of the bone. Further advancement of the clamp member 84 causes the tissue pad 88 to apply pressure on the bone or tissue.

Teeth or other friction means 90 may be disposed on the distal portion of the hook 24 to make contact with the distal side of the bone so that when the clamp member 84 extended, the device 20 is clamped or held in position relative to the bone. The contacting surface of the hook also may be modified or configured in the manner described above for the tissue pad.

FIG. 18 shows another embodiment of a clamping mechanism. The tubular clamp member 84 is slideably disposed or connected with the handle 22 of the device 20,70. The clamp member 84 may also include a lumen extending therethrough. A squeeze/finger grip 92 is connected with the handle 22 for advancing and retracting the clamp member 84 relative to the handle 22. When the squeeze grip 92 is moved toward the handle 22, the clamp member 84 may be moved or ratcheted distally thereby pressing the tissue pad 88 against the bone or other tissue. In this configuration, the clamp member functions like a come-along with detents and/or teeth. The squeeze grip 92 may be moved away from the handle 22 to move the clamp member 84 proximally, or a release button or spring or clip may be activated to permit the clamp member 84 to move proximally. Teeth or other friction means 90 may be disposed on the proximal side of the socket 78. With the clamp member 84 extended, the device 70 is held to the bone or other tissue between the tissue pad 88 and teeth 90 or socket 78.

Other embodiments of the clamping mechanism are further contemplated. For example, the guidance and positioning device 20,70 may include one or more inflatable members, such balloons. An inflatable balloon may be positioned along the hook at a location where the hook passes near the proximal surface of the tissue. That is, the balloon may be located at the proximal end of the curved portion of the hook. In a deflated configuration, the device may be properly positioned by the physician. The balloon may then be inflated to press against the proximal side of the tissue causing the distal end of the hook to press against the distal side of the tissue and thereby hold or lock the device in place. The balloon may be inflated with air, gas, or liquid. Inflation may be made manually with a hand pump, electrically with an electric pump or battery-operated pump, or pneumatically with a pressure cartridge. The balloon may also help guide the distal end of the hook into the proper position. Multiple balloons may be inflated and/or deflated together or separately to guide the hook. Also, the balloon(s) may be used to create space in tissue.

In another example, the device 20,70 may include a balloon at the distal end of the hook. Operation of the balloon may be similar to as previously described; however, in the current embodiment, the balloon may inflate to press against the distal side of the tissue causing the proximal portion of the hook (which may include a tissue pad or gripping teeth) to press against the proximal side of the tissue to thereby hold the device in position. Furthermore, two or more balloons may be used to position and hold the device relative to the tissue. The plurality of balloons may be located along the hook or guide channel and inflated together or individually to properly align and hold the device in place. In addition to holding the device relative to the tissue, the balloon or balloons may compress the tissue, tissue elements, and/or implant. With the tissue and/or implant compressed, a fastener or other implant may be positioned within the body.

Figure 19:
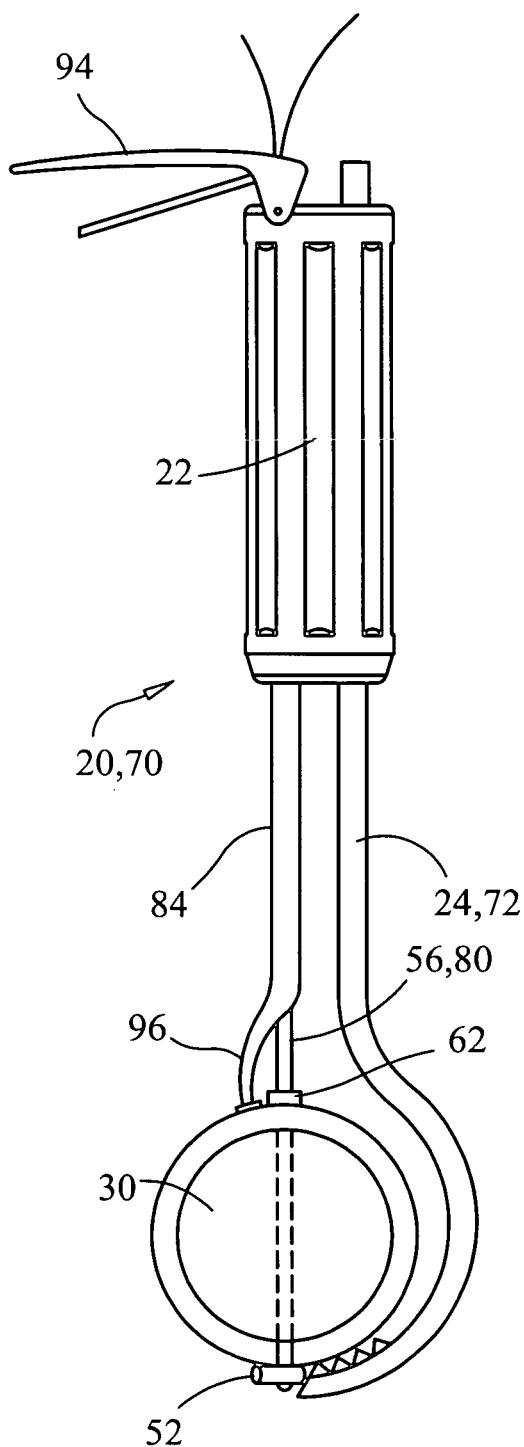
FIG. 19 shows an embodiment of a tensioning mechanism of the device.

As illustrated in FIG. 19, the device 20,70 may include a tensioning mechanism 94 to tension the suture 56 or fastening member 80. The tensioning mechanism 94 may be attached to the handle 22, tubular member 24, elongated member 72, or other component of the device 20,70. After the suture 56 or fastening member 80 is inserted through the passage in tissue, like a fractured bone 30, the tensioning mechanism 94 may pull and tension the suture 56 or fastening member 80 while a proximal fastener 62 is positioned to maintain the tension in the suture 56 or fastening member 80. The tensioning mechanism 94 may be, but is not limited to, two elements which pinch the suture 56 or fastening member 80 to pull it proximally or a spool which rotates to pull the suture 56 or fastening member 80. A tension gauge, strain gauge, read-out display, tension limiter, and/or an audio or visual tension indicator may be used to apply the proper tension to the suture or fastening member. Also, measurement of the tension may be accomplished with a spring, a radiofrequency emitting device, and/or a sensor such as an electrical sensor, flexible sensor, compressive sensor, piezoelectric sensor. Other examples of tension applicators are disclosed in U.S. Pat. No. 6,010,525 entitled "Method and Apparatus for Securing a Suture"; U.S. Pat. No. 6,447,516 entitled "Method of Securing Tissue"; and U.S. Pat. No. 6,635,073 entitled "Method of Securing Body Tissue." The above mentioned patents are hereby incorporated by reference.

As further shown in FIG. 19, the distal portion 96 of the tubular clamp member 84 may be offset or curved thereby exposing the suture 56 or fastening member 80 between the fractured bone 30 and clamp member 84. The tubular clamp member 84 may include a lumen extending therethrough with the lumen having an aperture at or near the proximal end of the offset portion 96 or the distal end of the straight section of the clamp member 84. The offset distal portion 96 allows a fastener 62 to be placed around the suture 56 or fastening member 80 adjacent to the proximal side of the bone 30. When the suture 56 or fastening member 80 is tensioned with the tensioning mechanism 94, the fastener 62 may be applied to maintain the tension in the suture 56 or fastening member 80.

Figure 29:
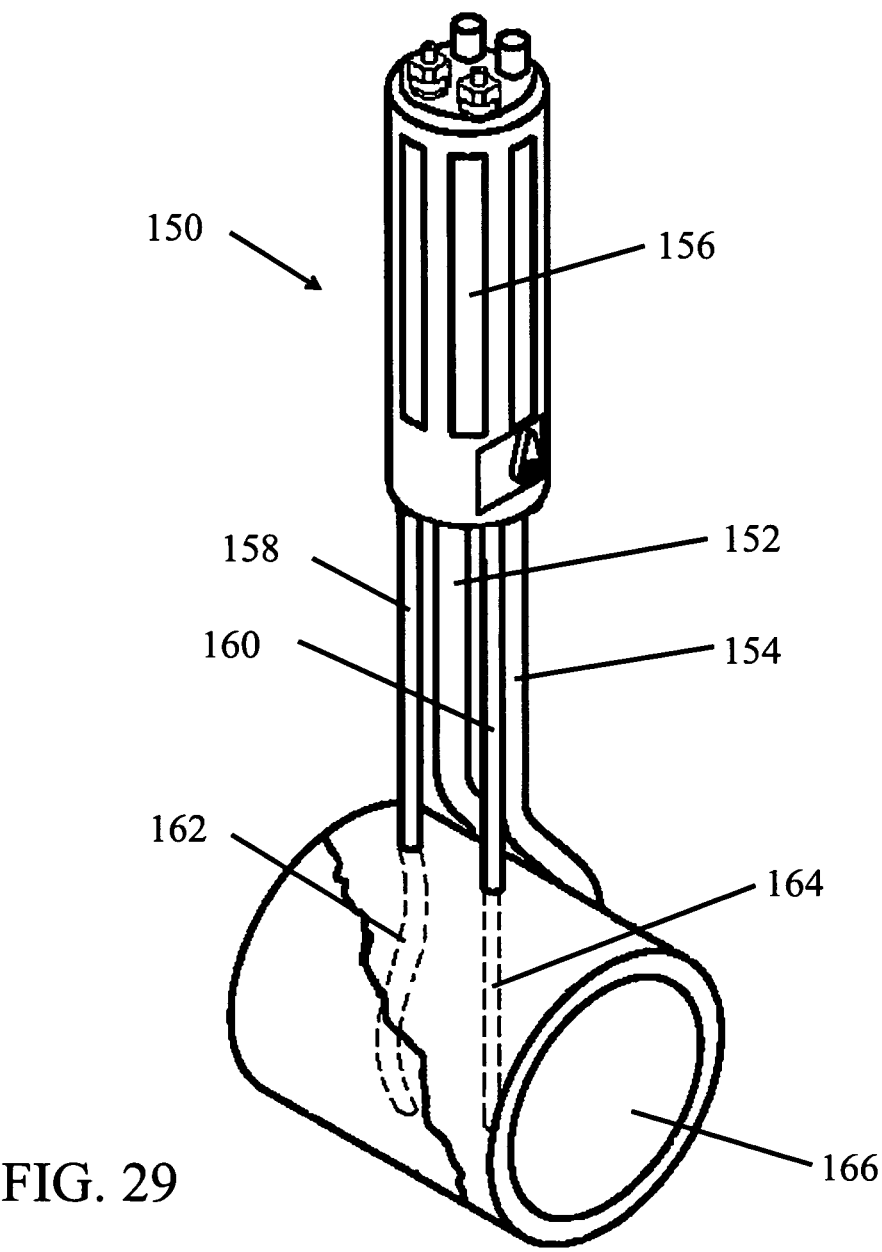
FIG. 29 snows another embodiment of the guidance and positioning device having multiple hooks and guide channels.

It is contemplated that the guidance and positioning device of the present invention may include more than one hook or elongated member for positioning multiple fasteners at the distal side of tissue. For example, as illustrated in FIG. 29, the device 150 may include two hooks or elongated members 152 and 154 attached to the handle 156 and positioned generally parallel to each other. The handle 156 may then include two guide channels, slots, or pins 158 and 160, each being aligned with one of the distal ends of the hook shaped tubular or elongated members. In this configuration, two passages 162 and 164 may be drilled in tissue, like a fractured bone 166, and two sutures or fastening members may be positioned through the passages, tensioned, and secured. One passage 162 may be non-linear while the other passage 164 may be linear. Having multiple hooks and guide channels or slots allows a physician to implant multiple fasteners thereby producing compression on the implant or tissue, enhancing the healing environment, and allowing for tissue ingrowth. The device with multiple hooks or pins may also be used to position other implants disclosed herein, such as adhesives, tissue scaffolds, medicaments, etc.

It is also contemplated that the device of the present invention may be disposable or may be sterilized after use and reused. The device may be partly disposable and partly reusable. For example, the handle may be reusable and the hook and/or guide channel may be disposable. Alternatively, the handle may be disposable. The device, its components, fasteners, drill bits, sutures, and other apparatus disclosed herein may be package in a kit. The kit may be set-up of a specific procedure, such as repair of a fractured bone, securing of an implant, approximating body tissue, etc.

Positioning Implants

The present invention not only provides an instrument and method for dynamic and rigid fastening of tissue, but it also provides for the guidance and positioning of an implant within the body. For example, the present invention may be utilized with tissue scaffolds as described in U.S. patent application Ser. No. 10/457,100 entitled "Scaffold and Method for Implanting Cells" by Peter M. Bonutti. Viable cells may be positioned on a support structure then implanted within a body. One or more blood vessels may be connected with the support structure to provide a flow of blood through the support structure. The devices and methods of the present invention may be used to guide and position the support structure within the body and fasten the scaffold to tissue or another implant by way of a sling support and/or strut. The above mentioned application is hereby incorporated by reference.

Furthermore, the present invention may be used in combination with a medical system for the administration of a pharmaceutical agent in vivo to a patient. The medical system may include an implant positionable in a body of a patient. A pharmaceutical agent may be disposed on the medical implant and at least partially coated with a reactive coating. The reactive coating acts to control the release of the pharmaceutical agent. An energy unit may be provided for transmitting an energy signal to the reactive coating, wherein the reactive coating reacts to the energy signal to control the release rate of the pharmaceutical agent. Additionally, the energy unit may also heat up the treatment site, locally increasing vascularity at the treatment site and allowing thermal necrosis of tissue. The localized increasing in temperature increases the permeability of the local tissue, allowing for an increased and more efficient adsorption of the pharmaceutical agent into the treatment site. Additionally, in response to localized increase in temperature, which can be perceived as physical damage or an infection to the local area, the local cells may release beneficial proteins, enzymes, hormones, etc.

In another embodiment, a pharmaceutical agent, drug, or medicament may be delivered within the body using the positioning device described herein. The hook and/or guide channel of the positioning device may conduct the passage of a medicament to a specific location within the body. The drug may be transported through the lumen of the hook or guide channel or, alternatively, may be placed on the exterior of the hook or guide channel. When the positioning device has been properly aligned, the medicament may be released in a constant stream or in a pulsatile manner. Examples of medicaments that may be used with the present invention include those disclosed throughout this application and, additionally, but not limited to, an anti-inflammatory agent, non-proliferative agent, anti-coagulant, anti-platelet agent, Tyrosine Kinase inhibitor, anti-infective agent, anti-tumor agent, anti-leukemic agent, and combinations thereof. One or more medicaments may be placed in one or more reservoirs which are in fluid communication with the positioning device. The reservoir may be physically separate from the device with tubing interconnecting the device and reservoir. Alternatively, the reservoir may be integrated into or attached to the positioning device. Release of the medicament may be achieved through manual operation such as with a plunger, air pressure, or valve or through electrical operation such as with a pump or valve. The medicament may be released from the positioning device or remotely away from the device as with a radiofrequency or signal emitting device.

It is contemplated that an adhesive may be delivered within the body in the way a medicament is delivered as described above. The adhesive could a polysaccharide based adhesive, fibrin adhesive, mollusc based adhesive, cyanoacrylate based adhesive, polymeric based adhesive, or other biocompatible adhesive. The adhesive could be thermally activated or pH activated. The adhesive could be a single part adhesive or a two part adhesive requiring both parts to activate the adhesive. The adhesive may also be hydrophilic or include hydrophilic material. The hydrophilic adhesive/ material may expand upon imbibing liquid, such as body fluid. In use, the adhesive may be delivered within the body to bond tissue together such as soft tissue to soft tissue, soft tissue to hard tissue, or hard tissue to hard tissue. For example, portions of a fractured bone may be adhered, a muscle may be bonded to other muscle or to a tendon, and a ligament may be adhered to another ligament, to muscle, and/or to bone. The adhesive may also be used to bond an implant with body tissue or to another implant. For example, a bone or joint replacement component may be adhered to another replacement component or to other bone, tissue scaffolding with cells may be bonded to other tissue or other scaffolding, and fasteners may be adhered to tissue or sutures.

In another embodiment, an energy sink, such as a pH sink, may be incorporated into a medical implant or be positioned separate from the medical implant. The pH sink is configured to absorb energy from the energy unit, releasing a chemical to either increase or decreasing the local pH. The change in local pH can either increase or decrease the degradation rate of a degradable polymer coating, which in turn can control the release rate of a pharmaceutical agent. The pH sink can be formed from calcium carbonate. Additionally, the localized change in pH created by the pH sink has beneficial effects, which include (but are not limited to): aiding in the alleviation of localized pain, fighting of local infections, and increasing vascular flow and permeability of vessels at the treatment site to control delivery of pharmaceutical agent.

For example, a localized increasing in pH increases the permeability of the local tissue, allowing for an increased and more efficient adsorption of the pharmaceutical agent into the treatment site. The energy sink may also be used to induce the release of beneficial enzymes, proteins, hormones, etc. from the cells in the treatment site. A localized increase in acidity and/or temperature can be perceived as a physical damage or an infection to the local area. In response, to the local cells may release beneficial proteins, enzymes, hormones, etc. The positioning device and method of the present invention may be used to guide and position a drug-eluting implant, a heat sink, or pH sink within the body.

The present invention may also be used with the disclosure of U.S. Provisional Patent Application No. 60/622,095 entitled "Devices and Methods for Stabilizing Tissue and Implants" by Peter M. Bonutti. The provisional application discloses various procedures for repairing, reconstructing, and stabilizing tissue and implants within the body. Examples of such tissue include bone, muscle, ligament, tendon, skin, organ, cartilage, and blood vessels. Examples of implants include an organ, partial organ grafts, tissue graft material (autogenic, allogenic, xenogenic, or synthetic), a malleable implant like a sponge, mesh, bag/sac/pouch, collagen, or gelatin, or a rigid implant made of metal, polymer, composite, or ceramic. Other implants include breast implants, biodegradable plates, metallic fasteners, rods, plates, screws, screw strips, spacers, cages, compliant bearing implants for one or more compartments of the knee, nucleus pulposus implant, stents, meniscal implants, tissue grafts, tissue scaffolds, biodegradable collagen scaffolds, polymeric or other biocompatible scaffolds, abdominal hernia meshes, cochlear implants, tracheal implants, small intestine submucosal grafts, TISSUEMEND scaffolds, prostheses, nanotechnology devices, sensors, emitters, radiofrequency emitting diodes, computer chips, RFID (radiofrequency identification) tags, adhesives, and sealants.

The guidance and positioning device of the present invention may be used to stabilize or fasten these implants and tissues. For example, the spine may be repaired or stabilized with fasteners, sutures, and cables to provide flexible or rigid reinforcement of the joints of the spine. Also, the nucleus pulposus of an intervertebral disc may be repaired or replaced using the guidance and positioning device of the present invention. For example, a prosthetic disc nucleus is positioned between two vertebral bodies and may be secured to surrounding tissue with fasteners and sutures. Additionally, the annulus may be repaired following a nucleus pulposus repair or replacement. The positioning device of the present invention may be used to position a fastener and suture on the internal side of the annulus. The suture may be pulled proximally through the annulus, tensioned, and secured with another fastener. Finally, the tissue alignment sleeves disclosed in the provisional application may be guided and positioned with the instrument and methods of the present invention. The above mentioned provisional application is incorporated herein by reference.

It is contemplated that the present invention may be utilized with the tracheal tube positioning apparatus of U.S. patent application Ser. No. 09/728,553 entitled "Tracheal Intubation" by Peter M. Bonutti. That application discloses positioning apparatus located relative to a patient's trachea by engaging the patient's trachea. Indicia on relatively movable sections of the positioning apparatus provide an indication of the distance between the patient's mouth and the patient's larynx. A flexible guide rod is moved through a distance corresponding to the distance between the patient's mouth and larynx, as determined by the positioning apparatus. A magnet is utilized to attract a leading end portion of the guide rod. A plurality of emitters may be disposed in an array around the patient's trachea. Outputs from the emitters are detected by a detector connected with the tracheal tube. The above mention patent application is hereby incorporated by reference.

Drill/Sleeve Combination

In another embodiment of the present invention, a drill bit and sleeve combination 100 is provided. In the following description, the drill bit and sleeve combination or system 100 is explained with reference to the fixation of two bones, like two portions of a fractured bone. It should be understood that the present embodiment may be utilized for fastening or securing tissue to tissue, an implant to tissue, or an implant to an implant.

Figure 20:
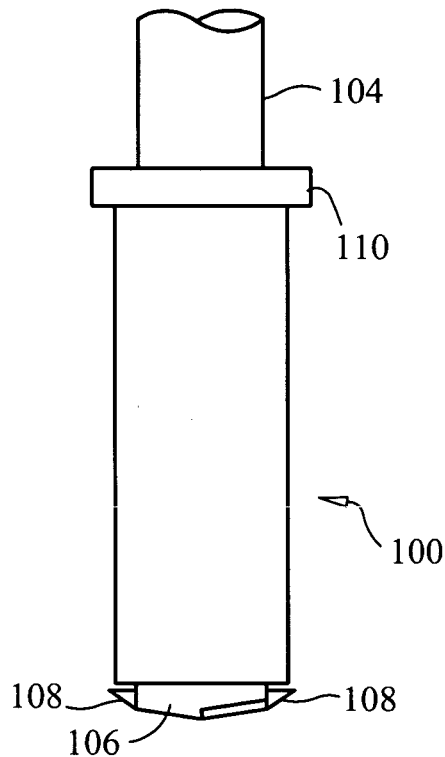
FIG. 20 illustrates a drill/sleeve combination in accordance with the present invention.

In FIG. 20 the system 100 includes a tubular member or sleeve 102 for aligning two portions of bone located on opposite sides of a fracture. A drill bit 104 extends through the longitudinal lumen of the sleeve 102. The distal portion 106 of the drill bit 104 has one or more pivoting blades 108. The system 100 may also include a pusher means 110 for inserting the sleeve 102 into the bone passage created by the drill bit 104. The pusher means 110 may be connected to the sleeve, bit, or the drill. Preferably, a portion of the pusher means 110 does not rotate with the bit or drill so that the sleeve 102 is not rotated as the pusher means 110 contacts the sleeve 102 during the drilling operation. Examples of the pusher means 110 include a washer-shaped member or donut-shaped member positioned over the bit or a U-shaped fork positionable around the shaft of the bit. The lower side of the pusher means 110 may be configured for contact with the proximal end of the sleeve, while the upper side of the pusher means 110 may be configured of applying a distal force with a hand, hammer, or press.

Figure 21:
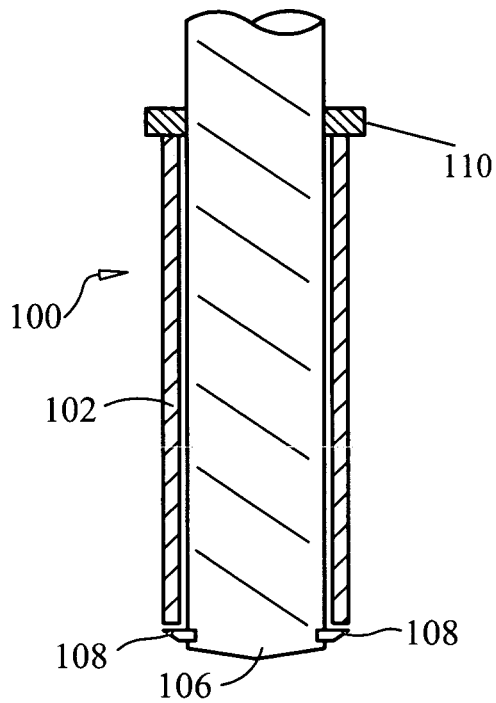
FIG. 21 is a cross sectional view of FIG. 20.

As seen in FIG. 21, the blades 108, when extended from the bit 104, increase the drilling diameter of the bit 104. The bone passage created by the drill bit 104 and the extended blades 108 has a diameter generally equal to the outside diameter of the sleeve 102. The blades 108, when retracted, pivot into or against the distal portion 106 of the bit 104. The diameter of the drill bit 104 with the blades 108 retracted is slightly less than the inside diameter of the sleeve 102.

The pivoting blades 108 of the system 100 may be connected with the distal portion 106 of the bit 104 in a variety of ways, but preferably, the blades 108 are pivotally attached to the bit 104. In one exemplary embodiment as seen in FIGS. 20 and 21, the blades 108 extend and retract along radial axes of the bit 104. The blades 108 may pivot downwardly or distally into an extended configuration and may pivot upwardly or proximally into a retracted configuration. In the retracted state, the blades 108 may be positioned within a groove or notch within the distal portion 106 of the bit 104. Furthermore, the blades 108 may be spring loaded to normally reside in the retracted configuration. When the drill bit 104 is rotated with a drill, the centrifugal force generated by the drill may cause the blades 108 to pivot into the extended configuration. Once in the extended position, the blades 108 may be locked into position to allow drilling or cutting of the bone.

In another exemplary embodiment, the blades 108 may be manually pivoted distally and proximally. A pin or shaft may extend along the center of the drill bit 104 with the distal end of the pin in contact with the blades 108. As the pin moved longitudinally, the blades 108 may extend and retract. The proximal portion of the pin may include a lever or other means for moving or advancing the pin along the center axis of the bit 104.

It is further contemplated that the blades 108 may be extended and retracted radially in and out of the distal portion of the bit 104 along a linear path instead of being pivoted as previously described. In this embodiment, the blades 108 may extend with centrifugal force and retract with a spring-like mechanism or may be manually extended and retracted with a pin or shaft along the central axis of the bit 104. Furthermore, other embodiments of the blades are contemplated. For example, the blades may be generally arch-shaped to conform to the outside circumference of the bit. The distal ends of the blades may be pivotally attached to the bit allowing the blades to extended radially outward for maximum cutting diameter or retract against the outer surface of the bit to minimize the bit diameter.

Figure 22:
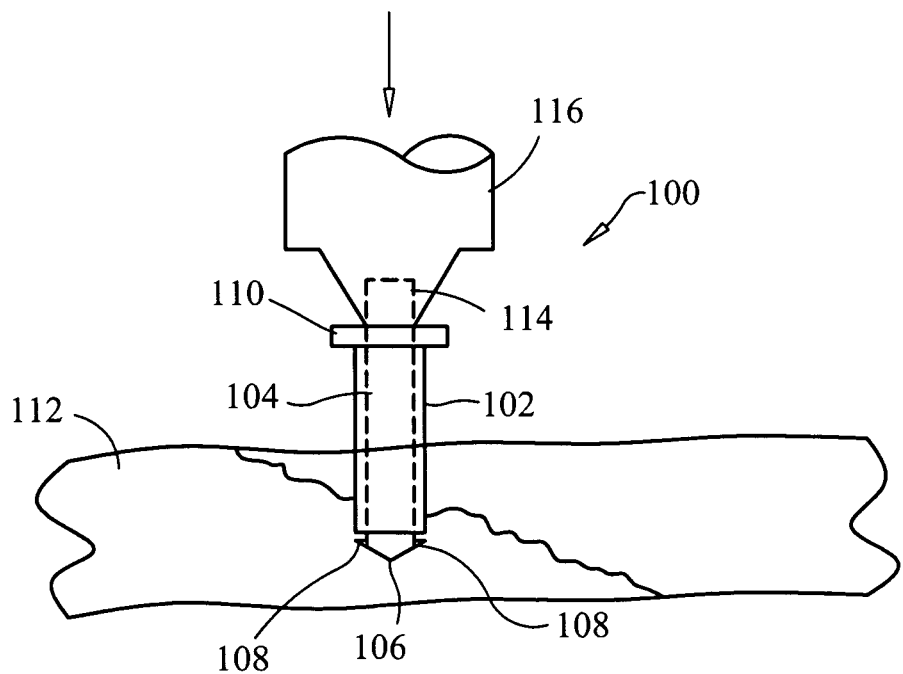
FIG. 22 shows the drill/sleeve combination in use to repair a fractured bone.
Figure 23:
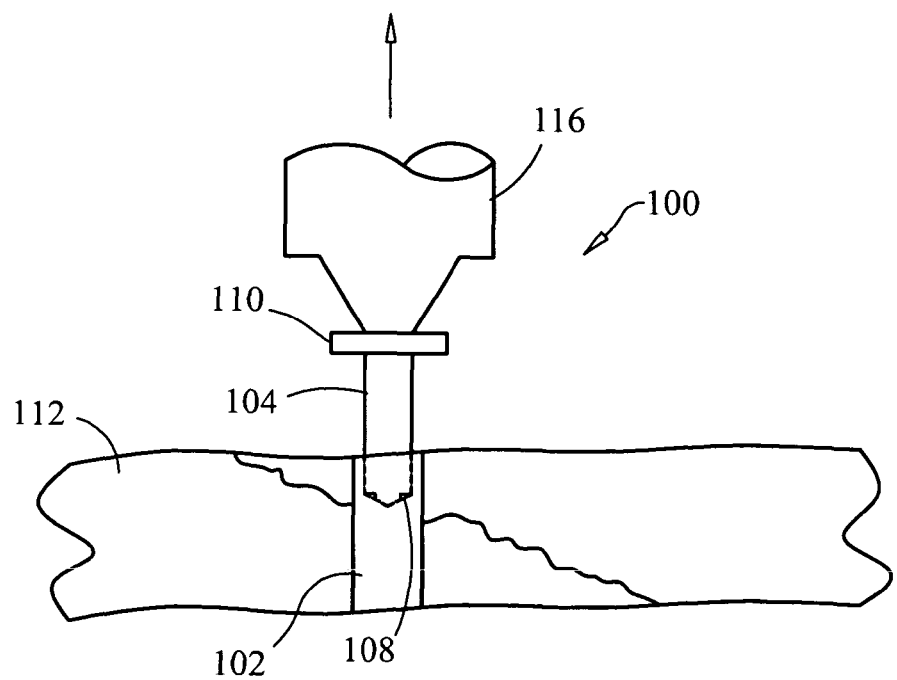
FIG. 23 illustrates the sleeve positioned across the fracture of the bone.

FIGS. 22 and 23 illustrate the drill bit and sleeve system 100 in use to repair a fractured bone 112. The drill bit 104 is inserted into the lumen of the sleeve 102. The distal portion 106 of the bit 104 and the pivoting blades 108 extend beyond the distal end of the sleeve 102. Preferably, the amount of bit 104 extending from distal end of the sleeve 102 is minimized to prevent damage to soft tissue of the distal side of the bone 112. The proximal portion of the bit or shank 114 extends from the proximal end of the sleeve 102 and is connected to a drill 116. The pivoting blades 108, located beyond the distal end of the sleeve 102, are in the extended configuration. The bit 104 is rotated and advanced distally through the fractured bone 112. As the bit 104 advances and creates a passage in the bone 112, the sleeve 104 is moved distally into the passage with the pusher means 110. The sleeve 102 is tight or snug within the passage since the diameter of the passage is generally equal to the outside diameter of the sleeve 102. When the sleeve 102 is in its proper position securing the bone portions 118 and 120 of the fractured bone 112, and the drill bit 104 may be removed from the lumen of the sleeve 102. The bit 104 may be pulled from the lumen of the sleeve 102 because the blades 108 may be positioned in the retracted configuration giving the drill bit 104 a diameter generally smaller than the diameter of the lumen of the sleeve 102. With the sleeve 102 in place, the bone is compressed, and the fracture is stabilized.

Figure 24:
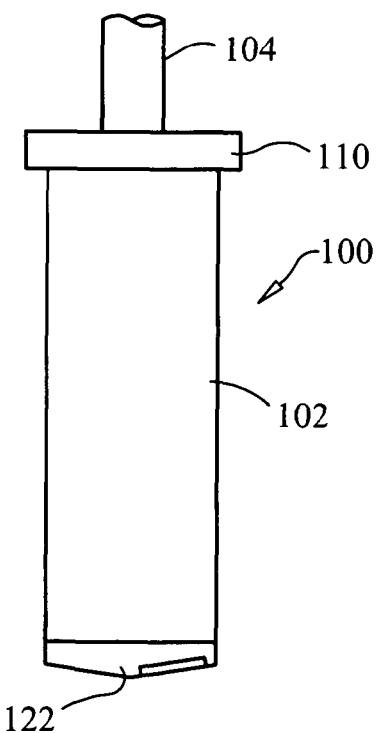
FIG. 24 shows another exemplary embodiment of the drill/sleeve combination.
Figure 25:
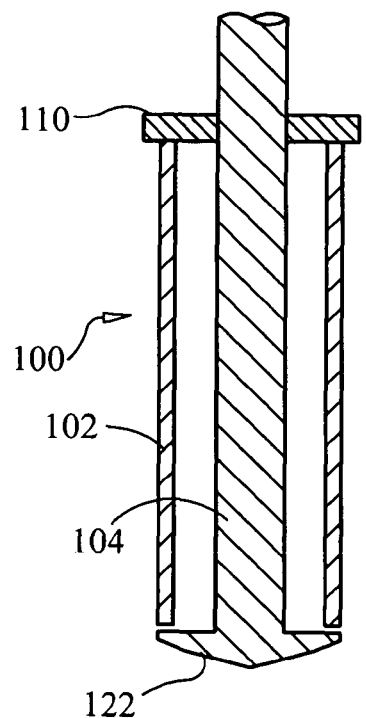
FIG. 25 is a cross sectional view of FIG. 24.

In another embodiment of the present invention, the drill bit and sleeve combination or system 100 is dimensioned and configured for transformation into a fastener. As shown in FIGS. 24 and 25, the system 100 includes the tubular member or sleeve 102, the pusher means 110, and a drill bit 104 with an expanding distal portion 122. The drill bit 104 extends through the lumen of the sleeve 102 with the distal portion 122 of the bit 104 extending beyond the distal end of the sleeve 102. The cutting diameter of the distal portion 122 of the bit 104 is generally equal to the outside diameter of the sleeve 102. In this embodiment, the distal portion 122 of the bit 104 does not include pivoting cutting blades. However, the distal portion 122 does include means for expansion to a diameter greater than the cutting diameter.

Figure 26:
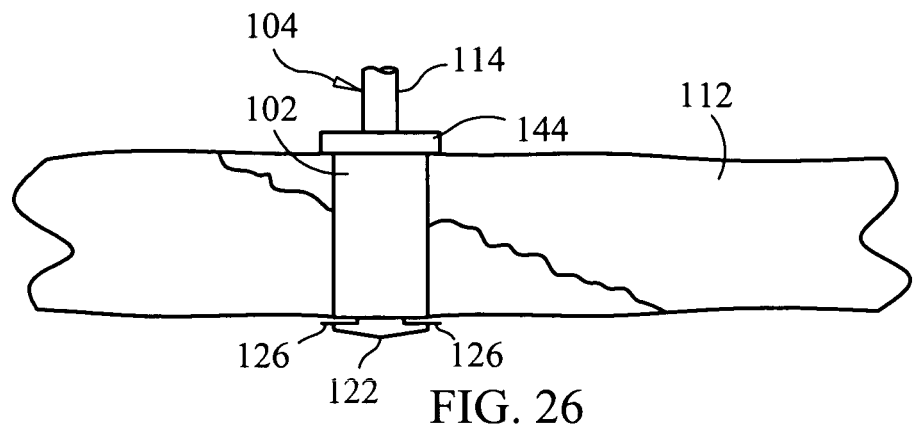
FIG. 26 illustrates the drill/sleeve combination functioning as a fastener.
Figure 27:
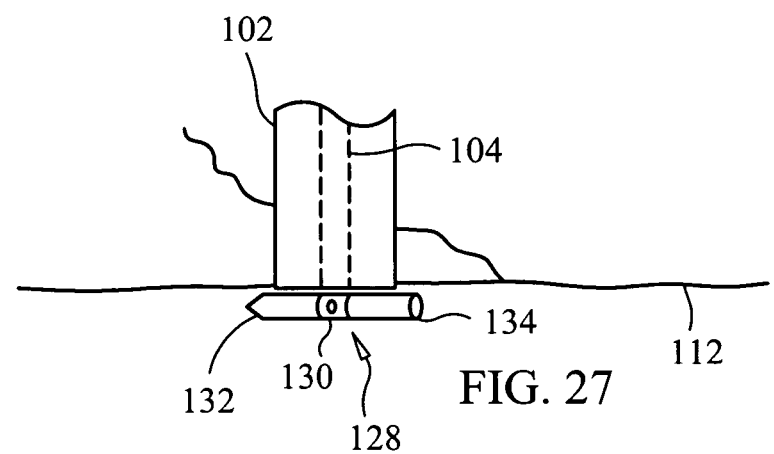
FIG. 27 shows an exemplary distal portion of the fastener.
Figure 28:
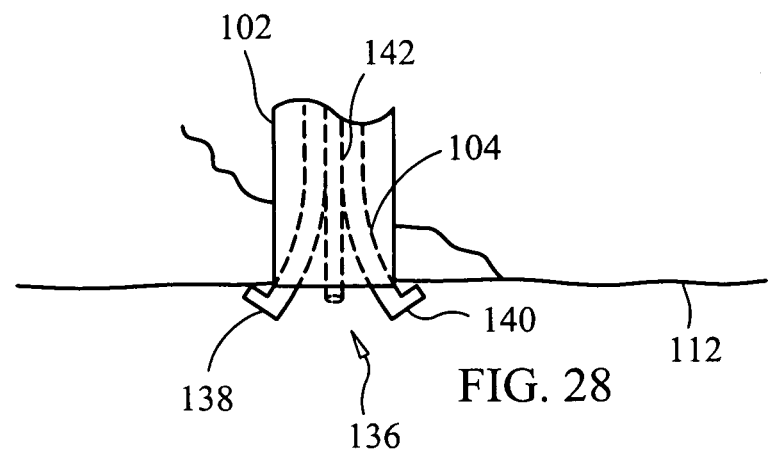
FIG. 28 illustrates another exemplary distal portion of the fastener.

Some examples of expansion means are shown in FIGS. 26-28. In FIG. 26 the expansion means includes one or more mechanically extending barbs 126 from the distal portion 122 of the bit 104. When extended or expanded, the barbs 126 increase the overall diameter of the drill bit 104. The barbs 126 may extend to the outside diameter of the sleeve 102, but preferably the barbs 126 extend beyond the outside edge of the sleeve 102. Most preferably, the barbs 126 extend over or into the distal side of the fractured bone 112. In the expanded configuration, the drill bit 104 is prevented from being pulled proximally out of the sleeve 102.

In FIG. 27, the expansion means includes a distal portion 128 of the drill bit 104 which pivots. In a first orientation during a drilling procedure, the distal portion 128 of the bit 104 is generally in-line with rest of the drill bit 104. After drilling, the distal portion 128 of the bit 104 is rotated about a pivot point into a second orientation. In the second orientation, the distal portion 128 is generally perpendicular to the rest of the drill bit 104. As a result, the end sections 132 and 134 of the pivoted distal portion 128 of the bit 104 extend beyond the outer diameter of the sleeve 102. Preferably, the end sections 132 and 134 extend over or into the distal side of the fractured bone 112 to prevent the bit 104 from being pulled from the sleeve 102.

In FIG. 28, the expansion means includes a distal portion 136 of the bit 104 which has two or more longitudinal sections 138 and 140 that are biased radially outward. The longitudinal sections 138 and 140 may be normally biased outward but held together by the lumen of the sleeve 102 when drilling through the bone 112. Alternatively, the longitudinal sections 138 and 140 may be normally in a non-biased configuration. After the passage is drilled in the bone 112, a plunger 142 within the drill bit 104 may be moved distally biasing the longitudinal sections 138 and 140 radially outward. With the longitudinal sections 138 and 140 biased, the distal portion 136 of the bit 104 may extend over or into the distal side of the fractured bone 112 to secure the bit 104 within the sleeve 102 and bone passage.

The drill bit and sleeve system 100 which transforms into a fastener may be utilized to secure various tissue and implants. Generally, in use, the drill bit 104 is inserted into the lumen of the sleeve 102 with the distal portion of the bit 104 extending beyond the distal end of the sleeve 102. The proximal portion of the bit or shank 114 extends from the proximal end of the sleeve 102 and connects to a drill. The bit 104 is rotated and advanced distally through the fractured bone 112. As the bit 104 advances and creates a passage in the bone 112, the sleeve 102 is moved distally into the passage with the pusher means 110. When the sleeve 102 is in its proper position connecting the two portions 118 and 120 of a fractured bone 112, the shank 114 of the drill bit 104 is removed from the drill. The distal portion of the bit 104, which extends just beyond the distal surface of the bone 112, is expanded with the expansion means.

Once expanded, the drill bit 104 is prevented from being pulled out of the bone passage. A retainer 144 may then be placed around the shank 114 of the bit 104 and moved distally to engage the proximal side of the bone 112. The retainer 144 is secured to the shank 114. With the distal portion of the bit expanded and the retainer connected to the shank, the drill bit (and the sleeve) is transformed into a fastener which holds the fractured bone in compression. It is also contemplated that the drill bit may be used without the sleeve so that the drill bit alone becomes a fastener.

The tubular member or sleeve of the present invention is generally tubular shaped having a wall with an inner surface and an outer surface. The inner surface defines a lumen which is dimensioned and configured for receiving a drill bit, suture, cable, K-wire, or similar device. The sleeve may include a slit through the tubular wall. The slit allows the sleeve to be decreased in diameter for implantation and increased in diameter after implantation for proper alignment of the implantation site. In a further embodiment, the sleeve may include two slits in the tubular wall thereby forming two semi-tubular members. The semi-tubular members may be placed separately at the implantation site then aligned to form a complete tubular member. In another embodiment, the tubular member is a solid member.

The tubular member or sleeve may be flexible to enable the tubular member to be inserted into a linear or nonlinear passage through the bone. The tubular member may be formed of metallic material, composite material, ceramic material, polymeric material, or combinations thereof. The sleeve may be made from a degradable, biodegradable, bioerodible, or bioabsorbable material, such as a polymer, composite, or ceramic. The tubular member may also include a therapeutic substance to form a composite tubular member, or the therapeutic substance may be coated onto the tubular member. Furthermore, therapeutic substances or graft material (autogenic, allogenic, xenogenic, or synthetic) may be packed into the sleeve.

Additionally, the outer surface of the tubular member may include a friction or gripping means. A portion of the outer surface of the tubular member may include threads, raised pebbles, bumps, raised ridges, or hills. In addition to a friction means on the outer surface of the tubular member, the wall of the sleeve may include openings for tissue ingrowth. The tubular member of the present invention is further described in U.S. Provisional Patent No. 60/622,095 entitled "Devices and Methods for Stabilizing Tissue and Implants," which is hereby incorporated by reference.

Guidance and Navigation

The guidance and positioning device of the present invention may be placed within the body of a patient with precise navigation. For example, one or more guide wires or k-wires may be utilized—one to hold the device in position and a second wire to drill or pass through tissue toward the distal end of the hook of the device. One of the guide wires or an additional wire can be used to pull a suture or fastener through the tissue. Alternatively, the positioning device may be positioned through an expanding retractor with percutaneous guidance.

Other navigation techniques for precise placement of the positioning device of the present invention include endoscopic guidance, magnetic resonance imaging, CT scan, ultrasound, fluoroscopy, X-ray, computer assisted navigation, magnetic guidance, electromagnetic guidance, radiofrequency guidance, optical guidance, and laser guidance. For example, the hook and/or guide channel of the positioning device may include a magnet, a radiofrequency emitter, or a thermal emitter/sensor. U.S. patent application Ser. No. 10/191,751 entitled "Method of Performing Surgery" discloses computer assisted navigation. In using computer assisted navigation with the present invention, emitters, receivers, and/or reflectors may be attached to the positioning device and/or tissue. The computer navigation system may utilize multiple separate registers which have optical feedback to a central unit. The computer navigation system may utilize electromagnetic or photo-optical feedback. U.S. Pat. No. 5,329,924 entitled "Sequential Imaging Apparatus"; U.S. Pat. No. 5,349,956 entitled "Apparatus and Method for Use in Medical Imaging"; and U.S. Pat. No. 5,542,423 entitled "Indexing Assembly for Joint Imaging" disclose further devices and methods for use in medical imaging. Also, the present invention may be performed using robotics, such as haptic arms or similar apparatus. The above mentioned patents and applications are hereby incorporated by reference.

It is contemplated that the device and method of the present invention be applied using minimally invasive incisions and techniques to preserve muscles, tendons, ligaments, bones, nerves, and blood vessels. A small incision(s) may be made adjacent the target area to be repaired, and a tube, delivery catheter, sheath, cannula, or expandable cannula may be used to perform the methods of the present invention. U.S. Pat. No. 5,320,611 entitled "Expandable Cannula Having Longitudinal Wire and Method of Use" discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening. The above mentioned patent is hereby incorporated by reference.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula. The above mentioned patents are hereby incorporated by reference.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

Furthermore, it is contemplated that the present invention may be used with bariatric surgery, gastric stapling, colorectal surgery, plastic surgery, gastroesophageal reflex disease (GERD) surgery, ligament reconstruction surgery (such as the anterior cruciate ligament, ACL), or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the device and method of the present invention.

It is further contemplated that the present invention may be used in conjunction with the devices and methods disclosed in U.S. Pat. No. 5,329,846 entitled "Tissue Press and System" and U.S. Pat. No. 5,269,785 entitled "Apparatus and Method for Tissue Removal." For example, an implant secured within the body using the present invention may include tissue harvested, configured, and implanted as described in the patents. The above mentioned patents are hereby incorporated by reference.

Additionally, it is contemplated that the device and method of the present invention may be used with heat bondable materials as disclosed in U.S. Pat. No. 5,593,425 entitled "Surgical Devices Assembled Using Heat Bondable Materials." For example, fasteners may include heat bondable material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above mentioned patent is hereby incorporated by reference.

Moreover, the device and method of the present invention may be used for the repair and reconstruction of a tubular pathway like a blood vessel, intestine, urinary tract, esophagus, or similar tubular body parts. For example, a blood vessel may be intentionally severed during a surgical operation, or the blood vessel may be damaged or torn as a result of an injury. Flexible fixation of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the positioning device of the present invention may be used then to approximate the damaged portion of the vessel.

Radiofrequency Identification

The devices, fasteners, and other apparatus disclosed herein may include RFID (radiofrequency identification) tags. Moreover, any surgical device, described herein or not, such as surgical instruments, implants, trays, sponges, screws, bolts, plates, knives, scalpels, etc. may include RFID emitting chips. RFID provides for inventory control before, during, and after surgery. Objects with RFID chips/tags which are located under sterile drapes or within sterile containers may be easily located without having to break the sterile environment. Also, surgical devices and instruments stored in cabinets or placed in an operating room may be scanned with an RFID receiver to help technicians and nurses quickly identify location, type, and quantity. RFID chips/tags placed on surgical objects may save significant time and money during surgery and inventory. Furthermore, matching RFID chips/tags may be placed on an instrument/device and on the tray which holds the device. Using the RF scanner/transmitter, the correct placement of the device can be determined. It is further contemplated that the kits previously described may include RFID chips/tags placed on the container and the components therein.

Surgical Tools

In another exemplary embodiment, the guidance and positioning device of the present invention may be used with pneumatic operated surgical instruments. For example, a gas-powered drill may be couple with the channel guide and/or handle of the positioning device. A surgeon may operate the drill by activating a switch to start the fluid of gas which rotates an air motor thereby rotating a drill bit. The drill may be connected to a compressed gas source with tubing. However, preferably, the drill includes a connecting port for attaching a gas cartridge or canister. Such a drill would be free from electrical and battery power and free from encumbering wires and hoses. The gas cartridge may be sized to fit within the drill body or attached externally on the drill body. The cartridge may be refillable or disposable. In addition to the drill being gas-powered, the clamping mechanism of the positioning device may be gas-powered. By activating the flow of gas, the clamp may be moved to engage and compress tissue and/or an implant, holding the tissue and/or implant in place until fasteners may be inserted. It is further contemplated that other surgical tools, such as saws, shavers, reamers, grinders, etc., may include gas cartridges as previously described. These gas-powered tools may also include a microprocessor for control and feedback.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. An apparatus for positioning an implant relative to a fractured and main portion of a bone, the apparatus comprising:
   a handle;
   a delivery member extending through the handle fixable in a discrete position with respect to the handle, the delivery member having a generally straight proximal portion and a curved member, the curved member including a distal end configured for engaging at least a portion of the fractured portion of the bone;
   a guide channel extending through the handle, the guide channel including a longitudinal axis that is configured to substantially align with the distal end of the curved member, wherein the guide channel is configured to move with respect to the handle to position against the main portion of the bone to substantially approximate the fractured portion of the bone to the main portion of the bone, and wherein the guide channel is configured to receive at least a portion of a puncture member configured to move through at least one of the fractured portion and main portion of the bone; and
   a locking mechanism coupled to the handle and configured to secure the delivery member with respect to the handle;
   wherein the proximal portion of the delivery member and the guide channel are generally parallel, such that the delivery member and the guide channel can be passed through a single portal or incision.

2. The apparatus of claim 1, wherein the guide channel is further configured to receive at least one of a cannula and sleeve of a drill system, the at least one cannula and sleeve operable to link a passage in the bone created by the drill system with the guide channel.

3. The apparatus of claim 1, wherein the delivery member is configured for retaining an implant, wherein the implant is a fastener having a suture attached thereto.

4. The apparatus of claim 3, further including an elongated claw dimensioned for insertion through the guide channel, the elongated claw including a member configured to secure the suture.

5. The apparatus of claim 3, wherein the fastener is fabricated from an ultrasonically-bondable material.

6. The apparatus of claim 1, wherein the device is operable to compress the fractured portion of the bone and the main portion of the bone together, guide an implant through the fractured portion and main portion of the bone, and deliver the implant while retaining the compressed portions of the bone.

7. The apparatus of claim 1, wherein the puncture member is a drill system.

8. An apparatus for positioning an implant relative to two portions of body tissue, the apparatus comprising:
   a handle;
   a delivery member extending through the handle fixable in a discrete position with respect to the handle, the delivery member having a generally straight proximal portion and a curved member, the curved member including a distal end configured for engaging a portion of a first body tissue;
   a guide channel extending through the handle, the guide channel including a longitudinal axis that is configured to substantially align with the distal end of the curved member, wherein the guide channel is configured to move with respect to the handle to position against a portion of a second body tissue, wherein the delivery member and the guide channel are configured to compress the first body tissue and the second body tissue; and
   a locking mechanism coupled to the handle and configured to secure the delivery member with respect to the handle;
   wherein the proximal portion of the delivery member and the guide channel are generally parallel, such that the delivery member and the guide channel can be passed through a single portal or incision.

9. The apparatus of claim 8, wherein the guide channel is configured to receive at least a portion of a puncture member configured to move through the second body tissue to create a passage in the second body tissue.

10. The apparatus of claim 8, wherein the guide channel is configured to receive a fastener that is configured to move through a passage in the second body tissue while the delivery member and the guide channel compress the first body tissue and the second body tissue.

11. The apparatus of claim 8, wherein at least one of the first and second body tissues is hard body tissue.

12. The apparatus of claim 1, wherein the guide channel is configured to position against the main portion of the bone to substantially approximate the fractured portion of the bone to the main portion of the bone further comprises the guide channel is configured to position against the main portion of the bone to substantially compress or stabilize the fractured portion of the bone to the main portion of the bone.

* * * * *